US011723937B2

(12) United States Patent
Peng et al.

(10) Patent No.: US 11,723,937 B2
(45) **Date of Patent: *Aug. 15, 2023**

(54) REPLICATION-COMPETENT VESICULAR STOMATITIS VIRUSES

(71) Applicant: Mayo Foundation for Medical Education and Research, Rochester, MN (US)

(72) Inventors: Kah-Whye Peng, Rochester, MN (US); Stephen James Russell, Rochester, MN (US); Camilo Ayala Breton, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 515 days.

This patent is subject to a terminal disclaimer.

(21) Appl. No.: 16/807,610

(22) Filed: Mar. 3, 2020

(65) Prior Publication Data

US 2020/0206286 A1 Jul. 2, 2020

Related U.S. Application Data

(60) Continuation of application No. 15/864,217, filed on Jan. 8, 2018, now Pat. No. 10,610,553, which is a continuation of application No. 15/380,728, filed on Dec. 15, 2016, now Pat. No. 9,861,668, which is a division of application No. 14/395,388, filed as application No. PCT/US2013/030971 on Mar. 13, 2013, now Pat. No. 9,555,067.

(60) Provisional application No. 61/635,164, filed on Apr. 18, 2012.

(51) Int. Cl.

| | |
|---|---|
| ***A61K 35/766*** | (2015.01) |
| ***C12N 15/86*** | (2006.01) |
| ***C12N 7/00*** | (2006.01) |
| ***C07K 14/005*** | (2006.01) |
| *A61K 38/00* | (2006.01) |

(52) U.S. Cl.

CPC .......... *A61K 35/766* (2013.01); *C07K 14/005* (2013.01); *C12N 7/00* (2013.01); *C12N 15/86* (2013.01); *A61K 38/00* (2013.01); *C12N 2760/18422* (2013.01); *C12N 2760/20221* (2013.01); *C12N 2760/20222* (2013.01); *C12N 2760/20232* (2013.01); *C12N 2760/20271* (2013.01); *C12N 2810/6081* (2013.01); *C12N 2810/859* (2013.01)

(58) Field of Classification Search

None

See application file for complete search history.

(56) References Cited

U.S. PATENT DOCUMENTS

| | | | | |
|---|---|---|---|---|
| 9,555,067 | B2 | 1/2017 | Peng et al. | |
| 9,861,668 | B2 | 1/2018 | Peng et al. | |
| 10,610,553 | B2 * | 4/2020 | Peng | A61P 35/00 |
| 2003/0138457 | A1 | 7/2003 | Whitt et al. | |
| 2011/0052539 | A1 | 3/2011 | Stojdl et al. | |
| 2015/0079037 | A1 | 3/2015 | Peng et al. | |
| 2017/0157187 | A1 | 6/2017 | Peng et al. | |
| 2018/0214497 | A1 | 8/2018 | Peng et al. | |

FOREIGN PATENT DOCUMENTS

| | | |
|---|---|---|
| WO | WO 2008/037458 | 4/2008 |
| WO | WO 2008/135230 | 11/2008 |
| WO | WO 2012/031137 | 3/2012 |

OTHER PUBLICATIONS

Alvarez-Breckenridge et al., "Pharmacologic and Chemical Adjuvants in Tumor Virotherapy," Chem. Rev., 109(7):3125-3140, Jul. 2009.

Ayala-Breton et al., "Oncolytic Properties of a Vesicular Stomatitis/Measles Hybrid Virus," [powerpoint presentation] American Society of Gene & Cell Therapy, ASGCT 15th Annual Meeting, Philadelphia, PA, 22 pages, May 16-20, 2012.

Ayala-Breton et al., "Oncolytic properties of a vesicular stomatitis/measles virus hybrid," Molecular Therapy, 20(Supp. 1):S208-S209, Abstract 540, American Society of Gene & Cell Therapy, May 2012, 2 pages.

Ayala-Breton et al., "Retargeting Vesicular Stomatitis Virus Using Measles Virus Envelope Glycoproteins," Hum Gene Ther., 23(5):484-491, May 2012.

Cattaneo, "Paramyxovirus entry and targeted vectors for cancer therapy," PLoS Pathog., 6(6):e1000973, Jun. 24, 2010.

Chang et al., "Five Difference Anti-Prostate-specific Membrane Antigen (PSMA) Antibodies Confirm PSMA Expression in Tumor-Associated Neovasculature," Cancer Res., 59:3192-3198, Jul. 1999.

Clarke et al., "Synergistic Attenuation of Vesicular Stomatitis Virus by Combination of Specific G Gene Truncations and N Gene Translocations," J. Virol., 81:2056-2064, Feb. 2007.

Dingli et al., "Image-guided radiovirotherapy for multiple myeloma using a recombinant measles virus expressing the thyroidal sodium iodide symporter," Blood, 103:1641-1646, Mar. 2004.

European Communication Pursuant to Article 94(3) EPC in Application No. 13778612,5, dated Mar. 15, 2017, 5 pages.

European Search Report for Application No. 13778612.5, dated Nov. 9, 2015, 6 pages.

Funke et al., "Targeted Cell Entry of Lentiviral Vectors," Mol. Ther., 16:1427-1436, Aug. 2008.

Funke, "Targeted cell entry of lentiviral vectors," Dissertation, Frankfurt am Main, 9 pages, 2009.

(Continued)

*Primary Examiner* — James D Schultz

(74) *Attorney, Agent, or Firm* — Fish & Richardson P.C.

(57) ABSTRACT

This document provides methods and materials related to vesicular stomatitis viruses. For example, replication-competent vesicular stomatitis viruses, nucleic acid molecules encoding replication-competent vesicular stomatitis viruses, methods for making replication-competent vesicular stomatitis viruses, and methods for using replication-competent vesicular stomatitis viruses to treat cancer or infectious diseases are provided.

13 Claims, 22 Drawing Sheets

Specification includes a Sequence Listing.

(56) References Cited

OTHER PUBLICATIONS

GenBank® Accession No. AF235001.1, (GI No. 12642413), Mus musculus sodium iodide symporter NIS mRNA, complete cds), dated Feb. 1, 2001, 2 pages.
GenBank® Accession No. AF380353.1, (GI No. 14290144), Mus musculus sodium iodide symporter mRNA, complete cds, dated Jun. 5, 2001, 2 pages.
GenBank® Accession No. BC105047.1, (GI No. 85397519), *Homo sapiens* solute carrier family 5 (sodium iodide symporter), member 5, mRNA (cDNA clone MGC:132707 IMAGE:8144050), complete cds, dated Jul. 21, 2006, 3 pages.
GenBank® Accession No. BC105049, (GI No. 85397913), *Homo sapiens* solute carrier family 5 (sodium iodide symporter), member 5, mRNA (cDNA clone MGC:132709 IMAGE:8144052), complete cds, dated Jul. 21, 2006, 3 pages.
GenBank® Accession No. BC119395.1, (GI No. 111601321), Mus musculus interferon beta 1, fibroblast, mRNA (cDNA clone MGC:155711 IMAGE:8734144), complete cds, dated Aug. 9, 2006, 2 pages.
GenBank® Accession No. BC119397.1, (GI No. 111601034), Mus musculus interferon beta 1, fibroblast, mRNA (cDNA clone MGC:155713 IMAGE:8734146), complete cds, dated Aug. 9, 2006, 2 pages.
GenBank® Accession No. EU332920 (GI No. 186660456), Measles virus strain Halle phosphoprotein (P), V protein (P), and C protein (P) genes, complete cds, dated Dec. 31, 2008, 2 pages.
GenBank® Accession No. EU332925 (GI No. 186660430), Measles virus strain Edmonston matrix protein (M) mRNA, complete cds, dated Dec. 31, 2008, 2 pages.
GenBank® Accession No. EU332930 (GI No. 18660438), Measles virus strain Edmonston fusion protein (F) mRNA, complete cds, dated Dec. 31, 2008, 2 pages.
GenBank® Accession No. EU332935 (GI No. 186660446), Measles virus strain Edmonston hemagglutinin (H) mRNA, complete cds, dated Dec. 31, 2008, 2 pages.
GenBank® Accession No. FN339541 (GI No. 2985638460), Schistosoma japonicum isolate Anhui clone SJC_S008602, complete sequence, whole genome shotgun sequence, dated Apr. 11, 2009, 1 page.
GenBank® Accession No. FW339541.1 (GI No. 298563846), Oncolytic Rhabdovirus, dated Jun. 17, 2010, 3 pages.
GenBank® Accession No. NC_001560, (GI No. 9627229), Vesicular stomatitis Indiana virus, complete genome, dated Mar. 9, 2011, 7 pages.
GenBank® Accession No. NM_000453.2, (GI No. 164663746), *Homo sapiens* solute carrier family 5 (sodium/iodide cotransporter), member 5 (SLC5A5), mRNA, dated Feb. 5, 2012, 6 pages.
GenBank® Accession No. NM_002176.2 (GI No. 50593016), *Homo sapiens* interferon, beta 1, fibroblast (IFNB1), dated Mar. 10, 2012, 3 pages.
GenBank® Accession No. NM_010510.1 (GI No. 6754303), Mus musculus interferon beta 1, fibroblast (Ifnb1), mRNA, dated Mar. 24, 2012, 3 pages.
GenBank® Accession No. NM_019127, (GI No. 9506800). Rattus norvegicus interferon beta 1, fibroblast (Ifnb1), mRNA, dated Apr. 21, 2012, 2 pages.
GenBank® Accession No. NM_052983, (GI No. 158138504), Rattus norvegicus solute carrier family 5 (sodium/iodide cotransporter), member 5 (Slc5a5), mRNA, dated Mar. 4, 2012, 5 pages.
GenBank® Accession No. NM_053248.2,(GI No. 162138896), Mus musculus solute carrier family 5 (sodium iodide symporter), member 5 (Slc5a5), mRNA, dated May 26, 2012, 5 pages.
GenBank® Accession No. NM_214410, (GI No. 47523871), Sus scrofa solute carrier family 5 (sodium iodide symporter), member 5 (SLC5A5), mRNA, dated Aug. 25, 2012, 2 pages.
GenBank® Accession No. XM_524154, (GI No. 332853961), Predicted: Pan troglodytes solute carrier family 5 (sodium/iodide cotransporter), member 5 (SLC5A5), transcript variant X1, mRNA, dated Oct. 25, 2012, 3 pages.
GenBank® Accession No. XM_541946, (GI No. 545534201), Predicted: Canis lupus familiaris solute carrier family 5 (sodium/iodide cotransporter), member 5 (SLC5A5), transcript variant X2, mRNA, dated Dec. 2, 2011, 2 pages.
GenBank® Accession No. XM_581578.6 (GI No. 358412847), Predicted: Bos taurus solute carrier family 5 (sodium iodide symporter), member 5 (SLC5A5), mRNA, dated Nov. 29, 2011, 2 pages.
Goel et al., "Radioiodide imaging and radiovirotherapy of multiple myeloma using VSV-NIS, an attenuated vesicular stomatitis virus encoding the sodium iodide symporter gene," Blood, 110(7):2342-2350, Oct. 2007.
Hadac et al., "Reengineering paramyxovirus tropism," Virology, 329:217-225, Sep. 2004.
Hasegawa et al., "The Use of a Tropism-Modified Measles Virus in Folate Recceptor-Targeted Virotherapy of Ovarian Cancer," Clin. Cancer Res., 12(20):6170-6178, Oct. 2006.
International Preliminary Report on Patentability for PCT/US2013/030971, dated Oct. 30, 2014, 6 pages.
International Search Report and Written Opinion for PCT/US2013/030971, dated Jun. 27, 2013, 7 pages.
Jenks et al., "Safety studies on intrahepatic or intratumoral injection of oncolytic vesicular stomatitis virus expressing interferon-beta in rodents and nonhuman primates," Hum Gene Ther., 21(4):451-462, Apr. 2010.
Kelly et al., "Attenuation of Vesicular Stomatitis Virus Encephalitis through MicroRNA Targeting," J. Virol., 84(3):1550-62 Feb. 2010.
Lawson et al., "Recombinant vesicular stomatitis viruses from DNA," Proc. Natl. Acad. Sci. USA, 92:4477-4481 May 1995.
Liu et al., "Ablation of nectin4 binding compromises CD46 usage by a hybrid vesicular stomatitis virus/measles virus," J Virol., 88(4):2195-2204, Epub Dec. 11, 2013.
Liu et al., "Prostate-Specific Membrane Antigen Retargeted Measles Virotherapy for the Treatment of Prostate Cancer," Prostate, 69(10):1128-1141, Jul. 2009.
Liu et al., "Systemic therapy of disseminated myeloma in passively immunized mice using measles virus-infected cell carriers," Mol Ther., 18(6):1155-1164, Epub Mar. 16, 2010.
Majid et al., "Evaluating Replication-Defective Vesicular Stomatitis Virus as a Vaccine Vehicle," J. Virol., 80:6993-7008, Jul. 2006.
McKenna et al., "Immunogenicity study of glycoprotein-deficient rabies virus expressing simian/human immunodeficiency virus SHIV89.6P envelope in a rhesus macaque," J Virol., 78(24):13455-13459, Dec. 2004.
Myers et al., "Preclinical Pharmacology and Toxicology of Intravenous MV-NIS, an Oncolytic Measles Virus Administered With our Without Cyclophosphamide," Clin. Pharmacol. Ther., 82:700-710, Dec. 2007.
Nakamura et al., "Antibody-targeted cell fusion," Nat Biotechnol., 22(3):331-336, Epub Feb. 15, 2004.
Nakamura et al., "Rescue and propagation of fully retargeted oncolytic measles viruses," Nat. Biotechnol., 23(2):209-214, Feb. 2005.
Navaratnarajah et al., "Measles virus glycoprotein complex assembly, receptor attachment, and cell entry," Curr Top Microbiol Immunol., 329:59-76, 2009.
Nies and Spielberg, "Principles of Therapeutics," In Goodman & Gilman's The Pharmacological Basis of Therapeutics, eds. Hardman, et al., McGraw-Hill, NY, 1996, pp. 43-62.
Obuchi et al., "Development of Recombinant Vesicular Stomatitis Viruses That Exploit Defects in Host Defense to Augment Specific Oncolytic Activity," J. Virol., 77(16):8843-56, Aug. 2003.
Office Action in Japanese Application No. 2015-506998, dated Jan. 18, 2017, 12 pages (with English Translation).
Office Action in U.S. Appl. No. 14/204,768, dated Feb. 16, 2016, 11 pages.
Office Action in U.S. Appl. No. 14/395,388, dated May 19, 2016, 8 pages.
Office Action in U.S. Appl. No. 14/395,388, dated Sep. 11, 2015, 8 pages.
Okuma et al., "Analysis of the Molecules Involved in Human T-cell Leukaemia Virus Type 1 Entry by a Vesicular Stomatitis Virus Pseudotype Bearing its Envelope Glycoproteins," J Gen Virol., 82(4):821-830, Apr. 2001.

(56) References Cited

OTHER PUBLICATIONS

Ong et al., "Oncolytic measles virus targets high CD46 expression on multiple myeloma cells," Exp. Hematol., 34(6):713-720, Jun. 2006.
Opyrchal et al., "Effective radiovirotherapy for malignant gliomas by using oncolytic measles virus strains encoding the sodium iodide symporter (MV-NIS)," Hum Gene Ther., 23(4):419-427, Epub Mar. 9, 2012.
Roche et al., "Structures of vesicular stomatitis virus glycoprotein: membrane fusion revisited," Cell. Mol. Life Sci., 65: 1716-1728 Jan. 2008.
Sabin and Olitsky, "Influence of Host Factors on Neuroinvasiveness of Vesicular Stomatitis Virus," J. Exp. Med., 67:229-249, Jan. 1938.
Schnell et al., "Foreign glycoproteins expressed from recombinant vesicular stomatitis viruses are incorporated efficiently into virus particles," Proc Natl Acad Sci U S A, 93:11359-11365, Oct. 1996.
Tatsuo et al., "Virus Entry is a Major Determinant of Cell Tropism of Edmonston and Wild-Type Strains of Measles Virus as Revealed by Vesicular Stomatitis Virus Pseudotypes Bearing Their Envelope Proteins," J. Virol., 74(9):4139-4145, May 2000.
Vongpunsawad et al., "Selectively Receptor-Blind Measles Viruses: Identification of Residues Necessary for SLAM- or CD46-Induced Fusion and Their Localization on a New Hemagglutinin Structural Model," J. Virol., 78:302-313, Jan. 2004.

* cited by examiner

| Name | Sequence | Size (nt) | |
|---|---|---|---|
| *pCG-F FWD* | GACTCAGCAA GCGGCCGCCA CCGGGAATCC CAGAATCA | 38 | (SEQ ID NO: 1) |
| *RVS* | TCGATCAGTG GCTCGAGGCA TGCCTACCGA TATTGTTCGG CCAGAGGGA | 49 | (SEQ ID NO: 2) |
| *pCG-H FWD* | GTCATCAGTG GCATGCTATG AAAAAAACTA ACAGATATCA ACTTAGGGTG CAAGATCATC GATA | 64 | (SEQ ID NO: 3) |
| *RVS* | TCGATCAGTG GGCATGCTGA TATCTGTTAG TTTTTTTCAT AAACCACTTG GACCCTACGT TTTTC | 65 | (SEQ ID NO: 4) |

SEQUENCE LISTING

```
<160> NUMBER OF SEQ ID NOS: 4

<210> SEQ ID NO 1
<211> LENGTH: 38
<212> TYPE: DNA
<213> ORGANISM: Measles virus

<400> SEQUENCE: 1

gactcagcaa gcggccgcca ccgggaatcc cagaatca                          38


<210> SEQ ID NO 2
<211> LENGTH: 49
<212> TYPE: DNA
<213> ORGANISM: Measles virus

<400> SEQUENCE: 2

tcgatcagtg gctcgaggca tgcctaccga tattgttcgg ccagaggga              49


<210> SEQ ID NO 3
<211> LENGTH: 64
<212> TYPE: DNA
<213> ORGANISM: Measles virus

<400> SEQUENCE: 3

gtcatcagtg gcatgctatg aaaaaaacta acagatatca acttagggtg caagatcatc  60

gata                                                               64


<210> SEQ ID NO 4
<211> LENGTH: 65
<212> TYPE: DNA
<213> ORGANISM: Measles virus

<400> SEQUENCE: 4
```

-continued

```
tcgatcagtg ggcatgctga tatctgttag tttttttcat aaaccacttg gaccctacgt     60

ttttc                                                                 65
```

REPLICATION-COMPETENT VESICULAR STOMATITIS VIRUSES

CROSS-REFERENCE TO RELATED APPLICATIONS

This application is a continuation of U.S. application Ser. No. 15/864,217, filed Jan. 8, 2018 (now U.S. Pat. No. 10,610,553), which is a continuation of U.S. application Ser. No. 15/380,728 (now U.S. Pat. No. 9,861,668), filed Dec. 15, 2016, which is a divisional of U.S. application Ser. No. 14/395,388 (now U.S. Pat. No. 9,555,067), filed Oct. 17, 2014, which is a national Stage application under 35 U.S.C. § 371 of International Application No. PCT/US2013/030971, filed Mar. 13, 2013, which claims the benefit of U.S. Provisional Application Serial No. 61/635,164, filed Apr. 18, 2012. The disclosures of the prior applications are considered part of (and are incorporated by reference in) the disclosure of this application.

STATEMENT AS TO FEDERALLY SPONSORED RESEARCH

This invention was made with government support under CA129193 awarded by the National Institutes of Health. The government has certain rights in the invention.

TECHNICAL FIELD

This document relates to methods and materials involved in making and using replication-competent vesicular stomatitis viruses. For example, this document relates to replication-competent vesicular stomatitis viruses, nucleic acid molecules, methods for making replication-competent vesicular stomatitis viruses, and methods for using replication-competent vesicular stomatitis viruses to treat cancer or infectious diseases.

BACKGROUND INFORMATION

Vesicular stomatitis virus (VSV) is a member of the Rhabdoviridae family. The VSV genome is a single molecule of negative-sense RNA that encodes five major polypeptides: a nucleocapsid (N) polypeptide, a phosphoprotein (P) polypeptide, a matrix (M) polypeptide, a glycoprotein (G) polypeptide, and a viral polymerase (L) polypeptide.

SUMMARY

This document provides methods and materials related to replication-competent vesicular stomatitis viruses. For example, this document provides replication-competent vesicular stomatitis viruses, nucleic acid molecules encoding replication-competent vesicular stomatitis viruses, methods for making replication-competent vesicular stomatitis viruses, and methods for using replication-competent vesicular stomatitis viruses to treat cancer or infectious diseases such as HIV.

As described herein, vesicular stomatitis viruses can be designed to have a nucleic acid molecule that encodes a VSV N polypeptide, a VSV P polypeptide, a VSV M polypeptide, a Paramyxovirus F polypeptide (e.g., a morbillivirus F polypeptide such as a measles virus F polypeptide), a Paramyxovirus H polypeptide (e.g., a morbillivirus H polypeptide such as a measles virus H polypeptide), and a VSV L polypeptide. Such a nucleic acid molecule can lack a functional VSV G polypeptide and/or lack the nucleic acid sequence that encodes a full-length VSV G polypeptide. For example, a vesicular stomatitis virus provided herein can be designed to have a nucleic acid molecule that encodes a VSV N polypeptide, a VSV P polypeptide, a VSV M polypeptide, a Paramyxovirus F polypeptide (e.g., a morbillivirus F polypeptide such as a measles virus F polypeptide), a Paramyxovirus H polypeptide (e.g., a morbillivirus H polypeptide such as a measles virus H polypeptide), and a VSV L polypeptide and lacks the ability to encode a functional VSV G polypeptide. In some cases, a vesicular stomatitis virus provided herein can be designed to have a nucleic acid molecule that encodes a VSV N polypeptide, a VSV P polypeptide, a VSV M polypeptide, a Paramyxovirus F polypeptide (e.g., a morbillivirus F polypeptide such as a measles virus F polypeptide), a Paramyxovirus H polypeptide (e.g., a morbillivirus H polypeptide such as a measles virus H polypeptide), and a VSV L polypeptide with the nucleic acid sequence encoding the Paramyxovirus F polypeptide and the Paramyxovirus H polypeptide being located in the position where the nucleic acid sequence encoding a full-length VSV G polypeptide is normally located in a wild-type vesicular stomatitis virus. In some cases, a vesicular stomatitis virus provided herein can be designed to have a nucleic acid molecule where the nucleic acid sequence encoding a VSV G polypeptide is replaced with nucleic acid that encodes a Paramyxovirus F polypeptide (e.g., a morbillivirus F polypeptide such as a measles virus F polypeptide) and a Paramyxovirus H polypeptide (e.g., a morbillivirus H polypeptide such as a measles virus H polypeptide).

As described herein, vesicular stomatitis virus/measles virus hybrids can be designed to have measles virus tumor selectivity and a rapid replication as observed with wild-type or parental vesicular stomatitis viruses. In some cases, a vesicular stomatitis virus/measles virus hybrid provided herein can be designed to have a preselected tropism. For example, Paramyxovirus (e.g., measles virus) F and/or H polypeptides having knocked out specificity for CD46, SLAM, and/or nectin-4 can be used. In such cases, a single chain antibody (scFv) or polypeptide ligand can be attached to, for example, the C-terminus of the Paramyxovirus (e.g., measles virus) H polypeptide. In such cases, the scFv or polypeptide ligand can determine the tropism of the vesicular stomatitis virus/measles virus hybrid. Examples of scFvs that can be used to direct vesicular stomatitis virus/measles virus hybrids to cellular receptors (e.g., tumor associated cellular receptors) include, without limitation, anti-EGFR, anti-αFR, and anti-PSMA scFvs. Examples of polypeptide ligands that can be used to direct vesicular stomatitis/measles virus hybrids include, without limitation, urokinase plasminogen activator uPA polypeptides, cytokines such as IL-13 or IL-6, single chain T cell receptors (scTCRs), echistatin polypeptides, and integrin binding polypeptides.

In some cases, a vesicular stomatitis virus/measles virus hybrid provided herein can have a nucleic acid molecule that includes a sequence encoding an interferon (IFN) polypeptide (e.g., a human IFN-β polypeptide), a sodium iodide symporter (NIS) polypeptide (e.g., a human NIS polypeptide), a fluorescent polypeptide (e.g., a GFP polypeptide), any appropriate therapeutic transgene (e.g., HSV-TK or cytosine deaminase), polypeptide that antagonizes host immunity (e.g., influenza NS1, HSVγ34.5, or SOCS1), or tumor antigen (e.g., cancer vaccine components). The nucleic acid encoding the IFN polypeptide can be positioned between the nucleic acid encoding the VSV M polypeptide and the nucleic acid encoding the VSV L polypeptide. Such a position can allow the viruses to express an amount of the IFN polypeptide that is effective to activate anti-viral innate immune responses in non-cancerous tissues, and thus alleviate potential viral toxicity, without impeding efficient viral replication in cancer cells. The nucleic acid encoding the NIS polypeptide can be positioned between the nucleic acid encoding the VSV M polypeptide and the VSV L polypeptide. Such a position of can allow the viruses to express an amount of the NIS polypeptide that (a) is effective to allow selective accumulation of iodide in infected cells, thereby allowing both imaging of viral distribution using radioisotopes and radiotherapy targeted to infected cancer cells, and (b) is not so high as to be toxic to infected cells. Positioning the nucleic acid encoding an IFN polypeptide between the nucleic acid encoding the VSV M polypeptide and the nucleic acid encoding the VSV L polypeptide and positioning the nucleic acid encoding a NIS polypeptide between the nucleic acid encoding the VSV M polypeptide and the VSV L polypeptide within the genome of a vesicular stomatitis virus can result in vesicular stomatitis viruses that are viable, that have the ability to replicate and spread, that express appropriate levels of functional IFN polypeptides, and that expression appropriate levels of functional NIS polypeptides to take up radio-iodine for both imaging and radio-virotherapy.

In general, one aspect of this document features a replication-competent vesicular stomatitis virus comprising an RNA molecule. The RNA molecule comprises, or consists essentially of, a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a Paramyxovirus F polypeptide (e.g., a morbillivirus F polypeptide such as a measles virus F polypeptide), a nucleic acid sequence that is a template for a positive sense transcript encoding a Paramyxovirus H polypeptide (e.g., a morbillivirus H polypeptide such as a measles virus H polypeptide), and a nucleic acid sequence that is a template for a positive sense transcript encoding a VSV L polypeptide, wherein the RNA molecule lacks a nucleic acid sequence that is a template for a positive sense transcript encoding a functional VSV G polypeptide. The Paramyxovirus H polypeptide can be a measles virus H polypeptide comprising Y481A and R533A amino acid substitutions with respect to a wild-type measles virus H polypeptide. The Paramyxovirus H polypeptide can comprise an amino acid sequence of a single chain antibody. The single chain antibody can be a single chain antibody directed to EGFR, αFR, or PSMA. The RNA molecule virus can comprise a nucleic acid sequence that is a template for a positive sense transcript encoding a NIS polypeptide.

In another aspect, this document features a composition comprising, or consisting essentially of, a replication-competent vesicular stomatitis virus comprising RNA molecule, wherein the RNA molecule comprises a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a Paramyxovirus F polypeptide (e.g., a morbillivirus F polypeptide such as a measles virus F polypeptide), a nucleic acid sequence that is a template for a positive sense transcript encoding a Paramyxovirus H polypeptide (e.g., a morbillivirus H polypeptide such as a measles virus H polypeptide), and a nucleic acid sequence that is a template for a positive sense transcript encoding a VSV L polypeptide, wherein the RNA molecule lacks a nucleic acid sequence that is a template for a positive sense transcript encoding a functional VSV G polypeptide. The Paramyxovirus H polypeptide can be a measles virus H polypeptide comprising Y481A and R533A amino acid substitutions with respect to a wild-type measles virus H polypeptide. The Paramyxovirus H polypeptide can comprise an amino acid sequence of a single chain antibody. The single chain antibody can be a single chain antibody directed to EGFR, αFR, or PSMA. The RNA molecule virus can comprise a nucleic acid sequence that is a template for a positive sense transcript encoding a NIS polypeptide.

In another aspect, this document features a nucleic acid molecule comprising a nucleic acid strand comprising, or consisting essentially of, a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a Paramyxovirus F polypeptide (e.g., a morbillivirus F polypeptide such as a measles virus F polypeptide), a nucleic acid sequence that is a template for a positive sense transcript encoding a Paramyxovirus H polypeptide (e.g., a morbillivirus H polypeptide such as a measles virus H polypeptide), and a nucleic acid sequence that is a template for a positive sense transcript encoding a VSV L polypeptide, wherein the nucleic acid strand lacks a nucleic acid sequence that is a template for a positive sense transcript encoding a functional VSV G polypeptide. The nucleic acid strand can comprise a nucleic acid sequence that is a template for a positive sense transcript encoding a NIS polypeptide. The NIS polypeptide can be a human NIS polypeptide.

In another aspect, this document features a method for treating cancer. The method comprises, or consists essentially of, administering a composition comprising replication-competent vesicular stomatitis viruses to a mammal comprising cancer cells, wherein the vesicular stomatitis viruses comprise an RNA molecule comprising a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a Paramyxovirus F polypeptide (e.g., a morbillivirus F polypeptide such as a measles virus F polypeptide), a nucleic acid sequence that is a template for a positive sense transcript encoding a Paramyxovirus H polypeptide (e.g., a morbillivirus H polypeptide such as a measles virus H polypeptide), and a nucleic acid sequence that is a template for a positive sense transcript encoding a VSV L polypeptide, wherein the RNA molecule lacks a nucleic acid sequence that is a template for a positive sense transcript encoding a functional VSV G polypeptide, wherein administration of the composition to the mammal is under conditions wherein the vesicular stomatitis viruses infect the cancer cells to form infected cancer cells, and wherein the number of cancer cells within the mammal is reduced following the administration. The mammal can be a human. The RNA molecule can comprise a nucleic acid sequence that is a template for a positive sense transcript encoding a NIS polypeptide. The NIS polypeptide can be a human NIS polypeptide.

In another aspect, this document features a method for inducing tumor regression in a mammal. The method comprises, or consists essentially of, administering a composition comprising replication-competent vesicular stomatitis viruses to a mammal comprising a tumor, wherein the vesicular stomatitis viruses comprise an RNA molecule comprising a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a Paramyxovirus F polypeptide (e.g., a morbillivirus F polypeptide such as a measles virus F polypeptide), a nucleic acid sequence that is a template for a positive sense transcript encoding a Paramyxovirus H polypeptide (e.g., a morbillivirus H polypeptide such as a measles virus H polypeptide), and a nucleic acid sequence that is a template for a positive sense transcript encoding a VSV L polypeptide, wherein the RNA molecule lacks a nucleic acid sequence that is a template for a positive sense transcript encoding a functional VSV G polypeptide, wherein administration of the composition to the mammal is under conditions wherein the vesicular stomatitis viruses infect tumor cells of the tumor to form infected tumor cells. The mammal can be a human. The RNA molecule can comprise a nucleic acid sequence that is a template for a positive sense transcript encoding a NIS polypeptide. The NIS polypeptide can be a human NIS polypeptide.

In another aspect, this document features a method for rescuing replication-competent vesicular stomatitis viruses from cells, wherein the vesicular stomatitis viruses comprise an RNA molecule comprising a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a Paramyxovirus F polypeptide (e.g., a morbillivirus F polypeptide such as a measles virus F polypeptide), a nucleic acid sequence that is a template for a positive sense transcript encoding a Paramyxovirus H polypeptide (e.g., a morbillivirus H polypeptide such as a measles virus H polypeptide), and a nucleic acid sequence that is a template for a positive sense transcript encoding a VSV L polypeptide, wherein the RNA molecule lacks a nucleic acid sequence that is a template for a positive sense transcript encoding a functional VSV G polypeptide. The method comprises (a) inserting nucleic acid encoding the RNA molecule into the cells under conditions wherein replication-competent vesicular stomatitis viruses are produced, and (b) harvesting the replication-competent vesicular stomatitis viruses.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 10A. Schematic representation of the full length infectious cDNA clone of VSV and the replacement of the G protein by MV-F and MV-H at positions 4 and 5, respectively. FIG. 10B. Primers used to flank F and H for PCR cloning of the genes into VSV-FH genome.

DETAILED DESCRIPTION

Figure 1A:
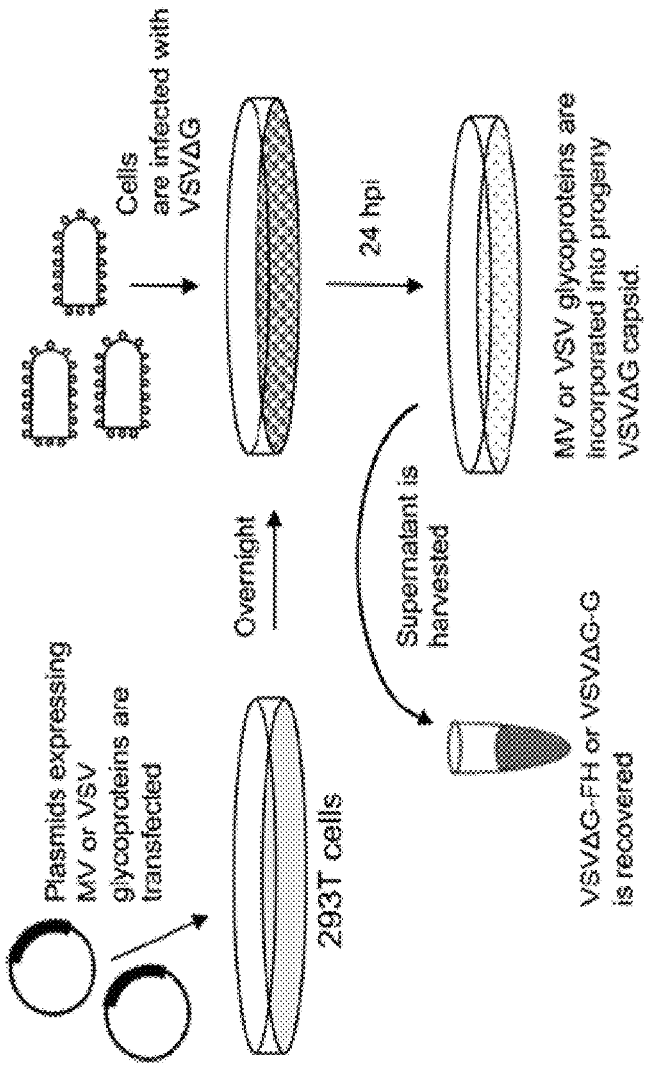
FIGS. 1A-1B. (A) Schematic representation of the protocol for pseudotyping VSVΔG with MV or VSV glycoproteins. The recovered supernatant contains VSVΔG-FH or VSVΔG-G vectors that can infect target cells and express viral proteins, but cannot produce viral progeny due to deletion of the VSV-G gene from the viral genome. (B) Titers of VSV pseudotyped with MV F/H glycoproteins bearing parental MV-H and F polypeptides or with truncated cytoplasmic tails (MV-HΔ24 or MV-FΔ30). Viral titers were determined on Vero-αHis cells. Results show representative data from two experiments.

This document provides methods and materials related to vesicular stomatitis viruses. For example, this document provides replication-competent vesicular stomatitis viruses, nucleic acid molecules encoding replication-competent vesicular stomatitis viruses, methods for making replication-competent vesicular stomatitis viruses, and methods for using replication-competent vesicular stomatitis viruses to treat cancer or infectious diseases.

As described herein, a vesicular stomatitis virus can be designed to have a nucleic acid molecule that encodes a VSV N polypeptide, a VSV P polypeptide, a VSV M polypeptide, a Paramyxovirus (e.g., a measles virus) F polypeptide, a Paramyxovirus (e.g., a measles virus) H polypeptide, and a VSV L polypeptide, and does not encode a functional VSV G polypeptide. It will be appreciated that the sequences described herein with respect to a vesicular stomatitis virus are incorporated into a plasmid coding for the positive sense cDNA of the viral genome allowing generation of the negative sense genome of vesicular stomatitis viruses. Thus, it will be appreciated that a nucleic acid sequence that encodes a VSV polypeptide, for example, can refer to an RNA sequence that is the template for the positive sense transcript that encodes (e.g., via direct translation) that polypeptide.

The nucleic acid encoding the Paramyxovirus (e.g., measles virus) F polypeptide and the Paramyxovirus (e.g., measles virus) H polypeptide can be positioned at any location within the VSV genome. In some cases, the nucleic acid encoding the Paramyxovirus (e.g., measles virus) F polypeptide and the Paramyxovirus (e.g., measles virus) H polypeptide can be positioned downstream of the nucleic acid encoding the VSV M polypeptide. For example, nucleic acid encoding a Paramyxovirus (e.g., measles virus) F polypeptide and nucleic acid encoding a Paramyxovirus (e.g., measles virus) H polypeptide can be positioned between nucleic acid encoding a VSV M polypeptide and nucleic acid encoding a VSV L polypeptide.

Any appropriate nucleic acid encoding a Paramyxovirus (e.g., measles virus) F polypeptide can be inserted into the genome of a vesicular stomatitis virus. For example, nucleic acid encoding a wild-type measles virus F polypeptide from an Edmonston strain can be inserted into the genome of a vesicular stomatitis virus. Examples of nucleic acid encoding measles virus F polypeptides can be inserted into the genome of a vesicular stomatitis virus include, without limitation, nucleic acid encoding a measles virus F polypeptide set forth in GenBank® Accession No. EU332930 (GI No. 18660438).

Any appropriate nucleic acid encoding a Paramyxovirus (e.g., measles virus) H polypeptide can be inserted into the genome of a vesicular stomatitis virus. For example, nucleic acid encoding a wild-type measles virus H polypeptide from an Edmonston strain can be inserted into the genome of a vesicular stomatitis virus. Examples of nucleic acid encoding measles virus H polypeptides can be inserted into the genome of a vesicular stomatitis virus include, without limitation, nucleic acid encoding a measles virus H polypeptide set forth in GenBank® Accession No. EU332935 (GI No. 186660446). In some cases, a nucleic acid encoding measles virus H polypeptides that lacks specificity for CD46, SLAM, nectin-4, or any combination thereof can be inserted into the genome of a vesicular stomatitis virus. For example, nucleic acid encoding a measles virus H polypeptide having Y481A (CD46 binding deleted) and R533A (SLAM binding deleted) can be inserted into the genome of a vesicular stomatitis virus. In some cases, a vesicular stomatitis virus/Paramyxovirus hybrid (e.g., a vesicular stomatitis virus/measles virus hybrid) provided herein can be designed to have a preselected tropism. For example, Paramyxovirus (e.g., measles virus) F and/or H polypeptides having knocked out specificity for CD46, SLAM, nectin-4, or any combination thereof can be used such that a scFv or polypeptide ligand can be attached to, for example, the C-terminus of the Paramyxovirus (e.g., measles virus) H polypeptide. In such cases, scFv or polypeptide ligand can determine the tropism of a vesicular stomatitis virus/Paramyxovirus hybrid (e.g., a vesicular stomatitis virus/measles virus hybrid). Examples of scFvs that can be used to direct vesicular stomatitis virus/Paramyxovirus hybrids (e.g., vesicular stomatitis virus/measles virus hybrids) to cellular receptors (e.g., tumor associated cellular receptors) include, without limitation, anti-EGFR, anti-αFR, anti-PSMA, anti-HER-2, anti-CD19, anti-CD20, or anti-CD38 scFvs. Examples of polypeptide ligands that can be used to direct vesicular stomatitis/Paramyxovirus hybrids (e.g., vesicular stomatitis virus/measles virus hybrids) include, without limitation, urokinase plasminogen activator uPA polypeptides, cytokines such as IL-13, single chain T cell receptors (scTCRs), echistatin polypeptides, and integrin binding polypeptides.

In some cases, the nucleic acid molecule of vesicular stomatitis virus provided herein can encode an IFN polypeptide, a fluorescent polypeptide (e.g., a GFP polypeptide), a NIS polypeptide, a therapeutic polypeptide, an innate immunity antagonizing polypeptide, a tumor antigen, or a combination thereof. Nucleic acid encoding an IFN polypeptide can be positioned downstream of nucleic acid encoding a VSV M polypeptide. For example, nucleic acid encoding an IFN polypeptide can be positioned between nucleic acid encoding a VSV M polypeptide and nucleic acid encoding a Paramyxovirus (e.g., a measles virus) F polypeptide or nucleic acid encoding a Paramyxovirus (e.g., a measles virus) H polypeptide. Such a position can allow the viruses to express an amount of IFN polypeptide that is effective to activate anti-viral innate immune responses in non-cancerous tissues, and thus alleviate potential viral toxicity, without impeding efficient viral replication in cancer cells.

Any appropriate nucleic acid encoding an IFN polypeptide can be inserted into the genome of a vesicular stomatitis virus. For example, nucleic acid encoding an IFN beta polypeptide can be inserted into the genome of a vesicular stomatitis virus. Examples of nucleic acid encoding IFN beta polypeptides that can be inserted into the genome of a vesicular stomatitis virus include, without limitation, nucleic acid encoding a human IFN beta polypeptide of the nucleic acid sequence set forth in GenBank® Accession No. NM_002176.2 (GI No. 50593016), nucleic acid encoding a mouse IFN beta polypeptide of the nucleic acid sequence set forth in GenBank® Accession Nos. NM_010510.1 (GI No. 6754303), BC119395.1 (GI No. 111601321), or BC119397.1 (GI No. 111601034), and nucleic acid encoding a rat IFN beta polypeptide of the nucleic acid sequence set forth in GenBank® Accession No. NM_019127.1 (GI No. 9506800).

Nucleic acid encoding a NIS polypeptide can be positioned downstream of nucleic acid encoding a Paramyxovirus (e.g., a measles virus) F polypeptide or nucleic acid encoding a Paramyxovirus (e.g., a measles virus) H polypeptide. For example, nucleic acid encoding a NIS polypeptide can be positioned between nucleic acid encoding a Paramyxovirus (e.g., a measles virus) F or H polypeptide and nucleic acid encoding a VSV L polypeptide. Such a position of can allow the viruses to express an amount of NIS polypeptide that (a) is effective to allow selective accumulation of iodide in infected cells, thereby allowing both imaging of viral distribution using radioisotopes and radiotherapy targeted to infected cancer cells, and (b) is not so high as to be toxic to infected cells.

Any appropriate nucleic acid encoding a NIS polypeptide can be inserted into the genome of a vesicular stomatitis virus. For example, nucleic acid encoding a human NIS polypeptide can be inserted into the genome of a vesicular stomatitis virus. Examples of nucleic acid encoding NIS polypeptides that can be inserted into the genome of a vesicular stomatitis virus include, without limitation, nucleic acid encoding a human NIS polypeptide of the nucleic acid sequence set forth in GenBank® Accession Nos. NM_000453.2 (GI No. 164663746), BC105049.1 (GI No. 85397913), or BC105047.1 (GI No. 85397519), nucleic acid encoding a mouse NIS polypeptide of the nucleic acid sequence set forth in GenBank® Accession Nos. NM_053248.2 (GI No. 162138896), AF380353.1 (GI No. 14290144), or AF235001.1 (GI No. 12642413), nucleic acid encoding a chimpanzee NIS polypeptide of the nucleic acid sequence set forth in GenBank® Accession No. XM_524154 (GI No. 114676080), nucleic acid encoding a dog NIS polypeptide of the nucleic acid sequence set forth in GenBank® Accession No. XM_541946 (GI No. 73986161), nucleic acid encoding a cow NIS polypeptide of the nucleic acid sequence set forth in GenBank® Accession No. XM_581578 (GI No. 297466916), nucleic acid encoding a pig NIS polypeptide of the nucleic acid sequence set forth in GenBank® Accession No. NM_214410 (GI No. 47523871), and nucleic acid encoding a rat NIS polypeptide of the nucleic acid sequence set forth in GenBank® Accession No. NM_052983 (GI No. 158138504).

The nucleic acid sequences of a vesicular stomatitis virus provided herein that encode a VSV N polypeptide, a VSV P polypeptide, a VSV M polypeptide, and a VSV L polypeptide can be from a VSV Indiana strain as set forth in GenBank® Accession Nos. NC_001560 (GI No. 9627229) or can be from a VSV New Jersey strain.

In one aspect, this document provides vesicular stomatitis viruses containing a nucleic acid molecule (e.g., an RNA molecule) having (e.g., in a 3' to 5' direction) a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a Paramyxovirus (e.g., a measles virus) F polypeptide, a nucleic acid sequence that is a template for a positive sense transcript encoding a Paramyxovirus (e.g., a measles virus) H polypeptide, and a nucleic acid sequence that is a template for a positive sense transcript encoding a VSV L polypeptide while lacking a nucleic acid sequence that is a template for a positive sense transcript encoding a functional VSV G polypeptide. Such vesicular stomatitis viruses can infect cells (e.g., cancer cells) and be replication-competent.

Any appropriate method can be used to insert nucleic acid (e.g., nucleic acid encoding a Paramyxovirus (e.g., a measles virus) F polypeptide, nucleic acid encoding a Paramyxovirus (e.g., a measles virus) H polypeptide, nucleic acid encoding an IFN polypeptide, and/or nucleic acid encoding a NIS polypeptide) into the genome of a vesicular stomatitis virus. For example, the methods described elsewhere (Schnell et. al., *PNAS,* 93:11359-11365 (1996), Obuchi et al., *J. Virol.,* 77(16):8843-56 (2003)); Goel et al., *Blood,* 110(7):2342-50 (2007)); and Kelly et al., *J. Virol.,* 84(3):1550-62 (2010)) can be used to insert nucleic acid into the genome of a vesicular stomatitis virus. Any appropriate method can be used to identify vesicular stomatitis viruses containing a nucleic acid molecule described herein. Such methods include, without limitation, PCR and nucleic acid hybridization techniques such as Northern and Southern analysis. In some cases, immunohistochemistry and biochemical techniques can be used to determine if a vesicular stomatitis virus contains a particular nucleic acid molecule by detecting the expression of a polypeptide encoded by that particular nucleic acid molecule.

In another aspect, this document provides nucleic acid molecules that encode a VSV N polypeptide, a VSV P polypeptide, a VSV M polypeptide, a Paramyxovirus (e.g., a measles virus) F polypeptide, a Paramyxovirus (e.g., a measles virus) H polypeptide, and a VSV L polypeptide, while lacking the ability to encode a functional VSV G polypeptide. For example, a nucleic acid molecule provided herein can be a single nucleic acid molecule that includes a nucleic acid sequence that encodes a VSV N polypeptide, a nucleic acid sequence that encodes a VSV P polypeptide, a nucleic acid sequence that encodes a VSV M polypeptide, a nucleic acid sequence that encodes a Paramyxovirus (e.g., a measles virus) F polypeptide, a nucleic acid sequence that encodes a Paramyxovirus (e.g., a measles virus) H polypeptide, and a nucleic acid sequence that encodes a VSV L polypeptide, while lacking a nucleic acid sequence that encodes a functional VSV G polypeptide.

In another aspect, this document provides nucleic acid molecules that encode a VSV N polypeptide, a VSV P polypeptide, a VSV M polypeptide, an IFN polypeptide, a Paramyxovirus (e.g., a measles virus) F polypeptide, a Paramyxovirus (e.g., a measles virus) H polypeptide, a NIS polypeptide, and a VSV L polypeptide, while lacking the ability to encode a functional VSV G polypeptide. For example, a nucleic acid molecule provided herein can be a single nucleic acid molecule that includes a nucleic acid sequence that encodes a VSV N polypeptide, a nucleic acid sequence that encodes a VSV P polypeptide, a nucleic acid sequence that encodes a VSV M polypeptide, a nucleic acid sequence that encodes an IFN polypeptide, a nucleic acid sequence that encodes a Paramyxovirus (e.g., a measles virus) F polypeptide, a nucleic acid sequence that encodes a Paramyxovirus (e.g., a measles virus) H polypeptide, a nucleic acid sequence that encodes a NIS polypeptide, and a nucleic acid sequence that encodes a VSV L polypeptide, while lacking the ability to encode a functional VSV G polypeptide.

The term "nucleic acid" as used herein encompasses both RNA (e.g., viral RNA) and DNA, including cDNA, genomic DNA, and synthetic (e.g., chemically synthesized) DNA. A nucleic acid can be double-stranded or single-stranded. A single-stranded nucleic acid can be the sense strand or the antisense strand. In addition, a nucleic acid can be circular or linear.

This document also provides method for treating cancer (e.g., to reduce tumor size, inhibit tumor growth, or reduce the number of viable tumor cells), methods for inducing host immunity against cancer, and methods for treating an infectious disease such as HIV or measles. For example, a vesicular stomatitis virus provided herein can be administered to a mammal having cancer to reduce tumor size, to inhibit cancer cell or tumor growth, to reduce the number of viable cancer cells within the mammal, and/or to induce host immunogeneic responses against a tumor. A vesicular stomatitis virus provided herein can be propagated in host cells in order to increase the available number of copies of that virus, typically by at least 2-fold (e.g., by 5- to 10-fold, by 50- to 100-fold, by 500- to 1,000-fold, or even by as much as 5,000- to 10,000-fold). In some cases, a vesicular stomatitis virus provided herein can be expanded until a desired concentration is obtained in standard cell culture media (e.g., DMEM or RPMI-1640 supplemented with 5-10% fetal bovine serum at 37° C. in 5% $CO_2$). A viral titer typically is assayed by inoculating cells (e.g., Vero cells) in culture.

Vesicular stomatitis viruses provided herein can be administered to a cancer patient by, for example, direct injection into a group of cancer cells (e.g., a tumor) or intravenous delivery to cancer cells. A vesicular stomatitis virus provided herein can be used to treat different types of cancer including, without limitation, myeloma (e.g., multiple myeloma), melanoma, glioma, lymphoma, mesothelioma, and cancers of the lung, brain, stomach, colon, rectum, kidney, prostate, ovary, breast, pancreas, liver, and head and neck.

Vesicular stomatitis viruses provided herein can be administered to a patient in a biologically compatible solution or a pharmaceutically acceptable delivery vehicle, by administration either directly into a group of cancer cells (e.g., intratumorally) or systemically (e.g., intravenously). Suitable pharmaceutical formulations depend in part upon the use and the route of entry, e.g., transdermal or by injection. Such forms should not prevent the composition or formulation from reaching a target cell (i.e., a cell to which the virus is desired to be delivered to) or from exerting its effect. For example, pharmacological compositions injected into the blood stream should be soluble.

While dosages administered will vary from patient to patient (e.g., depending upon the size of a tumor), an effective dose can be determined by setting as a lower limit the concentration of virus proven to be safe and escalating to higher doses of up to $10^{12}$ pfu, while monitoring for a reduction in cancer cell growth along with the presence of any deleterious side effects. A therapeutically effective dose typically provides at least a 10% reduction in the number of cancer cells or in tumor size. Escalating dose studies can be used to obtain a desired effect for a given viral treatment (see, e.g., Nies and Spielberg, "Principles of Therapeutics," In Goodman & Gilman's *The Pharmacological Basis of Therapeutics*, eds. Hardman, et al., McGraw-Hill, N Y, 1996, pp 43-62).

Vesicular stomatitis viruses provided herein can be delivered in a dose ranging from, for example, about $10^3$ pfu to about $10^{12}$ pfu (e.g., about $10^5$ pfu to about $10^{12}$ pfu, about $10^6$ pfu to about $10^{11}$ pfu, or about $10^6$ pfu to about $10^{10}$ pfu). A therapeutically effective dose can be provided in repeated doses. Repeat dosing is appropriate in cases in which observations of clinical symptoms or tumor size or monitoring assays indicate either that a group of cancer cells or tumor has stopped shrinking or that the degree of viral activity is declining while the tumor is still present. Repeat doses can be administered by the same route as initially used or by another route. A therapeutically effective dose can be delivered in several discrete doses (e.g., days or weeks apart) and in one embodiment, one to about twelve doses are provided. Alternatively, a therapeutically effective dose of vesicular stomatitis viruses provided herein can be delivered by a sustained release formulation. In some cases, a vesicular stomatitis virus provided herein can be delivered in combination with pharmacological agents that facilitate viral replication and spread within cancer cells or agents that protect non-cancer cells from viral toxicity. Examples of such agents are described elsewhere (Alvarez-Breckenridge et al., *Chem. Rev.,* 109(7):3125-40 (2009)).

Vesicular stomatitis viruses provided herein can be administered using a device for providing sustained release. A formulation for sustained release of vesicular stomatitis viruses can include, for example, a polymeric excipient (e.g., a swellable or non-swellable gel, or collagen). A therapeutically effective dose of vesicular stomatitis viruses can be provided within a polymeric excipient, wherein the excipient/virus composition is implanted at a site of cancer cells (e.g., in proximity to or within a tumor). The action of body fluids gradually dissolves the excipient and continuously releases the effective dose of virus over a period of time. Alternatively, a sustained release device can contain a series of alternating active and spacer layers. Each active layer of such a device typically contains a dose of virus embedded in excipient, while each spacer layer contains only excipient or low concentrations of virus (i.e., lower than the effective dose). As each successive layer of the device dissolves, pulsed doses of virus are delivered. The size/formulation of the spacer layers determines the time interval between doses and is optimized according to the therapeutic regimen being used.

Vesicular stomatitis viruses provided herein can be directly administered. For example, a virus can be injected directly into a tumor (e.g., a breast cancer tumor) that is palpable through the skin. Ultrasound guidance also can be used in such a method. Alternatively, direct administration of a virus can be achieved via a catheter line or other medical access device, and can be used in conjunction with an imaging system to localize a group of cancer cells. By this method, an implantable dosing device typically is placed in proximity to a group of cancer cells using a guidewire inserted into the medical access device. An effective dose of a vesicular stomatitis virus provided herein can be directly administered to a group of cancer cells that is visible in an exposed surgical field.

In some cases, vesicular stomatitis viruses provided herein can be delivered systemically. For example, systemic delivery can be achieved intravenously via injection or via an intravenous delivery device designed for administration of multiple doses of a medicament. Such devices include, but are not limited to, winged infusion needles, peripheral intravenous catheters, midline catheters, peripherally inserted central catheters, and surgically placed catheters or ports.

The course of therapy with a vesicular stomatitis virus provided herein can be monitored by evaluating changes in clinical symptoms or by direct monitoring of the number of cancer cells or size of a tumor. For a solid tumor, the effectiveness of virus treatment can be assessed by measuring the size or weight of the tumor before and after treatment. Tumor size can be measured either directly (e.g., using calipers), or by using imaging techniques (e.g., X-ray, magnetic resonance imaging, or computerized tomography) or from the assessment of non-imaging optical data (e.g., spectral data). For a group of cancer cells (e.g., leukemia cells), the effectiveness of viral treatment can be determined by measuring the absolute number of leukemia cells in the circulation of a patient before and after treatment. The effectiveness of viral treatment also can be assessed by monitoring the levels of a cancer specific antigen. Cancer specific antigens include, for example, carcinoembryonic antigen (CEA), prostate specific antigen (PSA), prostatic acid phosphatase (PAP), CA 125, alpha-fetoprotein (AFP), carbohydrate antigen 15-3, and carbohydrate antigen 19-4.

The invention will be further described in the following examples, which do not limit the scope of the invention described in the claims.

EXAMPLES

Example 1—Retargeting Vesicular Stomatitis Virus Using Measles Virus Envelope Glycoproteins Cells and Viruses Human cortical neuronal cells HCN-1A [American Type Culture Collection (ATCC), Manassas, Va.; CRL-10442] were maintained in medium as recommended by ATCC. CHO cell lines stably expressing CD46 (CHO-CD46), FR (CHO-FR), and EGFR (CHO-EGFR) were described elsewhere (Nakamura et al., *Nat. Biotechnol.,* 22:331-336 (2004)). The PC3 cells stably expressing PSMA (PC3-PSMA, originally named PC3-PIP) were provided by Dr. Michel Sadelain (Memorial Sloan-Kettering Cancer Center) (Chang et al., *Cancer Res.,* 59:3192-3198 (1999)). KAS 6/1 multiple myeloma cells were provided by Dr. Diane Jelinek (Mayo Clinic), and SKOV3ip.1 ovarian tumor cells were provided by Dr. Ellen Vitetta (University of Texas Southwestern Medical Center). KAS 6/1 cells were positive for CD46 and EGFR, but not αFR or PSMA. SKOV3ip.1 cells expressed CD46, EGFR, and αFR, but not PSMA. VSV (Indiana strain) with a deleted glycoprotein gene that was replaced by a green fluorescent protein (GFP) cDNA (VSVDG) was described elsewhere (Majid et al., *J. Virol.,* 80:6993-7008 (2006)). The Vero-αHis cells expressed a membrane-anchored single-chain antibody that recognizes a six histidine peptide (Nakamura et al., *Nat. Biotechnol.,* 23:209-214 (2005)).

Preparation of VSVΔG Pseudotypes

For pseudotyping VSVΔG with MV glycoproteins, three different types of plasmids were used: pCGF encoding parental Edmonston strain MV-F protein, pCGH encoding parental Edmonston strain MV-H protein, or pTNHaa (Nakamura et al., *Nat. Biotechnol.,* 22:331-336 (2004)) encoding a mutated MV-H protein, with two point mutations, Y481A and R533A, that block the interaction of MV-H with MV receptors CD46 and SLAM, respectively (Vongpunsawad et al., *J Virol.,* 78:302-313 (2004)). The plasmids encoding MV-H bearing an scFv directed against either αFR, EGFR, or PSMA (pTNHaa-αFR, pTNHaa-αEGFR, or pTNHaa-αPSMA) were used (Nakamura et al., *Nat. Biotechnol.,* 23:209-214 (2005); Hasegawa et al., *Clin. Cancer Res.,* 12:6170-6178 (2006); and Liu et al., *Prostate,* 69:1128-1141 (2009)). HEK-293T cells ($10^7$) were seeded in a 150-mm plate. Next day, 30 μg of pMD-G (plasmid encoding VSV-G protein) or 30 μg of a plasmid encoding MV-H protein (pCGH or pTNHaa) and 30 μg of a plasmid encoding MV-F protein (pCGF) were transfected into the cells using the calcium phosphate method. To avoid cell fusion due to the intracellular expression of MV-F and MV-H, 6.6 μg of fusion inhibitory peptide (FIP; Bachem, Americas Inc., Torrance, Calif.) per milliliter of culture medium was added to the cells 5 hours post transfection. The following day, transfected cells were infected for 3 hours with VSVΔG-G (VSVΔG pseudotyped with VSV-G protein) at a multiplicity of infection (MOI) of 3 in the presence of FIP. The virus inoculum was then removed, and cells were washed five times and incubated in OptiMEM (Invitrogen, Carlsbad, Calif.) plus FIP. After 24 hours of infection, cells and supernatant were freeze-thawed two times. Then, the supernatant was clarified (5 minutes at 1,600 rpm) and stored at −80° C. Titer for each virus was determined in Vero-αHIS cells using the standard $TCID_{50}$ titration method as described elsewhere for MV (Hadac et al., *Virology,* 329:217-225 (2004)). The viral supernatants were also concentrated by centrifugation for 5 minutes at 2,500 rpm in an Amicon Ultra-15 device with a 100,000 molecular weight cutoff (Millipore, Billerica, Mass.). The supernatant that did not pass through the filter was collected and stored at −80° C.

Immunoblotting for Viral Proteins

Protein lysates were fractionated by PAGE in 10% Tris-HCl Criterion precast gels (Bio-Rad, Hercules, Calif.) and transferred to a polyvinylidene difluoride membrane (Bio-Rad). Membranes were blocked with 5% non-fat milk in Tris-buffered saline (TBS)-Tween for 1 hour at room temperature, incubated with primary antibodies (polyclonal rabbit αMV-H (Hadac et al., *Virology,* 329:217-225 (2004)), polyclonal αVSV structural proteins (Jenks et al., *Hum. Gene Ther.,* 21:451-462 (2010)), washed five times with TBS-Tween, incubated with secondary antibody conjugated to peroxidase, and washed again five times. Signal was developed using Pierce ECL western blotting substrate kit (Thermo Scientific, Waltham, Mass.) following the conditions recommended by the manufacturer.

In Vivo Experiments

Six-week-old female CB17 ICR SCID mice (n=3 per group; Taconic Farms, Germantown, N.Y.) were irradiated with 150 Gy. 24 hours later, human myeloma KAS 6/1 cells were injected in the right flanks of the mice. When tumors reached 0.5 cm in diameter, mice received one intratumoral injection of VSV pseudotypes ($10^6$ $TCID_{50}$/100 μL). Two days post injection, mice were euthanized, and tumors were harvested. Tumor 5-μm cryosections were stained with DAPI, and GFP expression was analyzed using a Zeiss LSM 510 confocal microscope to detect areas of viral infection.

Results

Pseudotyping of VSV with MV-F and MV-H-scFv Polypeptides

Figure 1B:
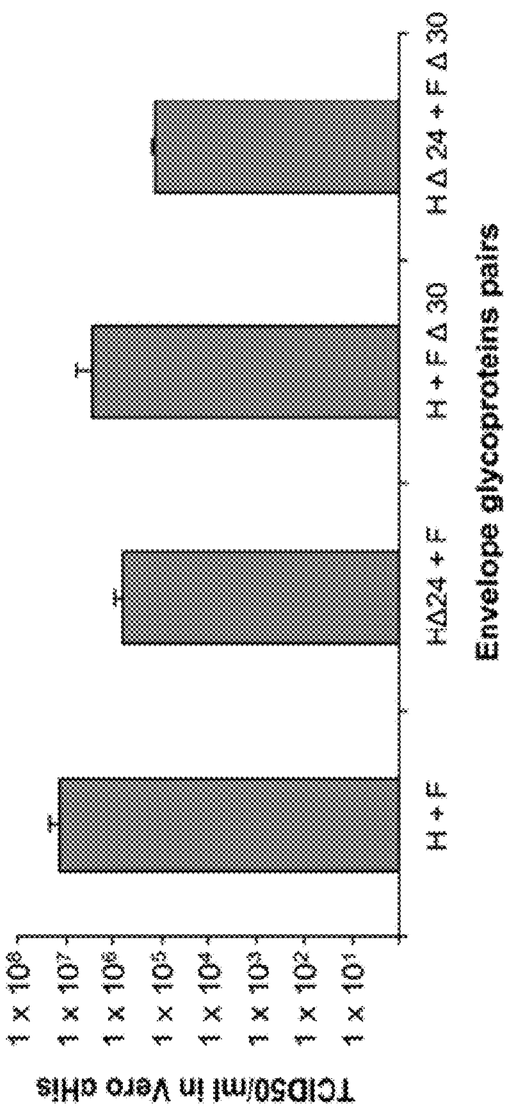

To pseudotype VSV with MV-F and MV-H polypeptides, 293T cells were first transfected with plasmids expressing MV-H and MV-F polypeptides and then were infected with a mutant VSV lacking the glycoprotein gene (FIG. 1). Progeny VSV were harvested from the supernatant and used. Due to deletion of the G gene from its genome, infectivity of the progeny VSV was driven exclusively by the incorporated MV-F and MV-H or H-scFv polypeptides.

To determine if MV-F or MV-H with shorter cytoplasmic tail could enhance their incorporation into VSV, VSV vectors were pseudotyped with parental MV-F/H or two mutant MV glycoproteins: MV-HΔ24 (MV-H with an N-terminal deletion of 24 amino acids) and MV-FΔ30 (with a complete deletion of the cytoplasmic tail except for the three membrane-proximal residues RGR). A 10- to 100-fold reduction in the viral titers of VSV pseudotyped with the truncated glycoproteins was observed (FIG. 1). Hence, for all subsequent studies, MV-F and MV-H with parental cytoplasmic tails were used.

VSV can be Pseudotyped with MV-F and MV-H Bearing a Single-Chain Antibody

To study the possible retargeting of VSV, the virus was pseudotyped with MV-F and either one of the following different versions of MV-H: parental Edmonston strain MVH, or MV-H bearing a single-chain antibody (H-scFv) directed to EGFR, αFR, and PSMA.

Figure 2:
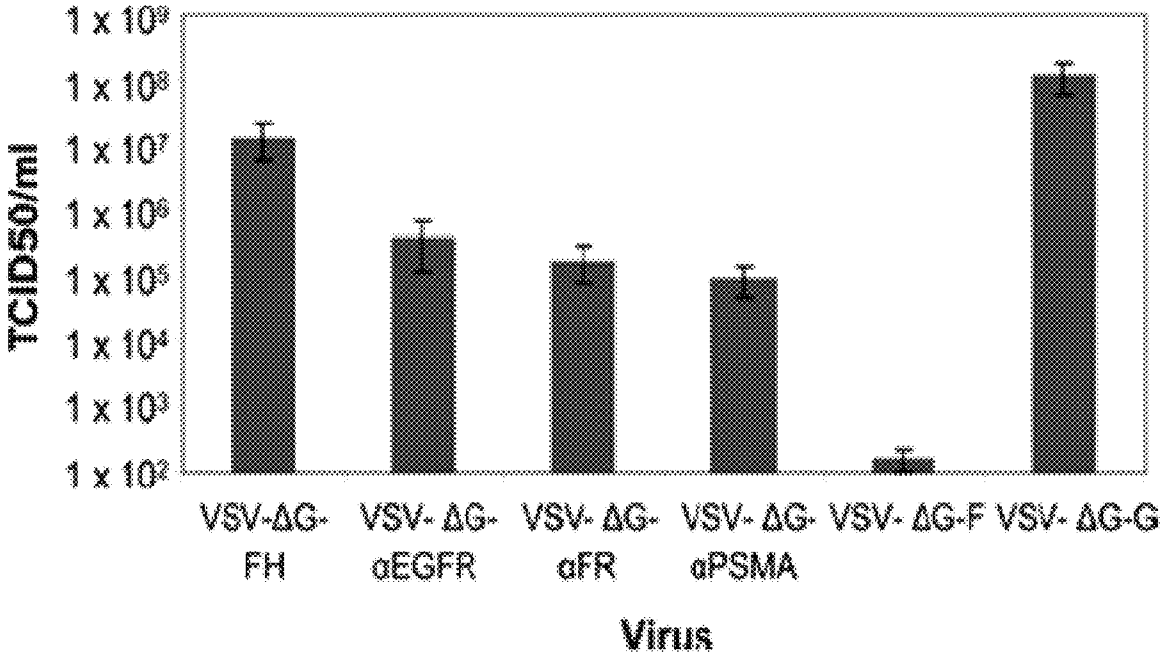
FIG. 2. Titers of retargeted VSV vectors. VSV were pseudotyped with VSV-G MV-F alone, or a combination of MV-F and MV-H with and without an scFv, and titers were determined on Vero-αHis cells. Results show average of four independent experiments.
Figure 3:
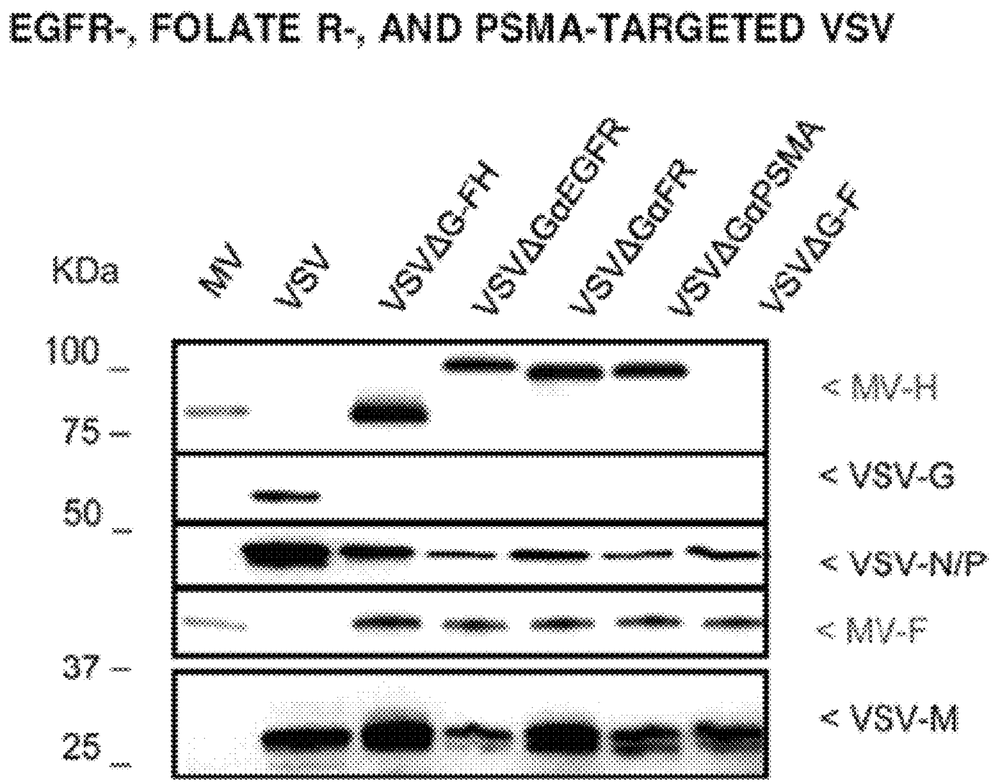
FIG. 3. Immunochemical analysis of VSV pseudotypes. Viral supernatants were purified, and polypeptides were fractionated by SDS-PAGE. MV and VSV polypeptides were detected with polyclonal anti-MV or anti-VSV antibodies.

Viral titers from the pseudotyped VSV are shown in FIG. 2. To demonstrate that the infection was due to MV-F/H pseudotyped VSV and not because of residual input VSVΔG-G virus, MV-H plasmid was not transfected into the cells to generate VSVΔG-F, and that virus had minimal infectivity (FIG. 2). In contrast, there was robust infection for other viral vectors, with titers ranging from $10^7$ $TCID_{50}$ for VSV pseudotyped with MV-H/F to $10^5$ $TCID_{50}$ for VSV pseudotyped with MV-H-scFv. Viral titers of pseudotyped vectors bearing retargeted envelopes could be increased to $1\times10^7$ when concentrated by ultrafiltration or sucrose cushion. To confirm the incorporation of the MV-H/F polypeptides into VSV virions, polypeptide lysates from the purified vector stocks were analyzed by immunoblot. As shown in FIG. 3, VSV-G was detected only in VSVΔG-G lysates. MV polypeptides, on the other hand, were observed in the lanes where lysates of VSVΔG-FH (and retargeted versions) were loaded.

VSV Infection can be Specifically Retargeted by MV Glycoproteins

Figure 4A:
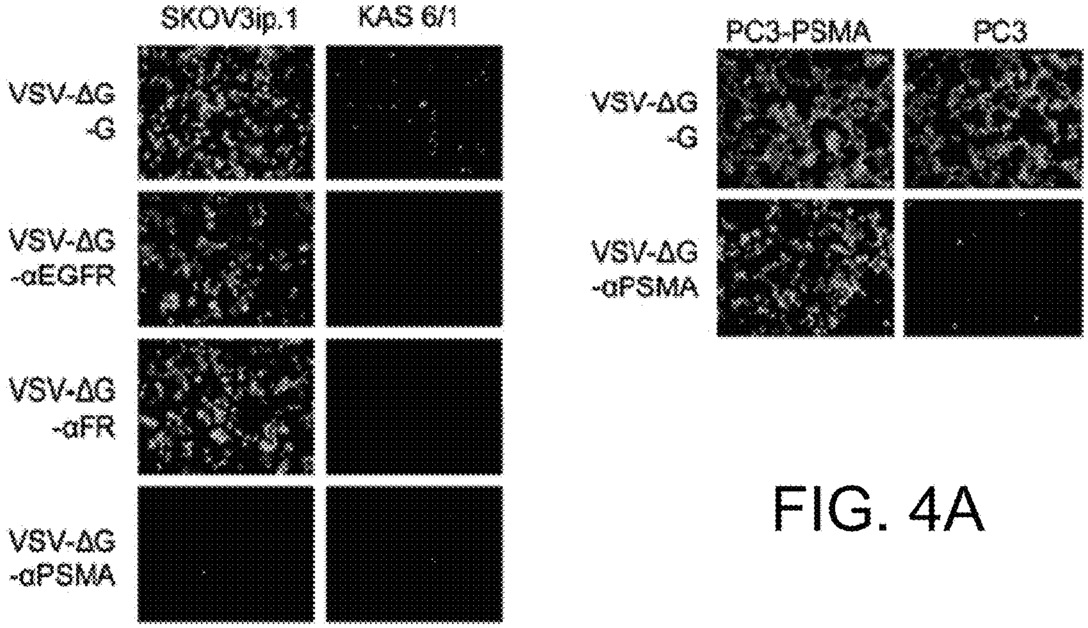
FIGS. 4A-4B. Retargeted VSV pseudotypes preferentially transduced receptor-positive cells. (A) Photographs of SKOV3.ip.1, KAS 6/1, PC3, and PC3-PSMA cells at 24 hours post transduction by retargeted VSV pseudotypes (MOI 3.0). GFP signal was observed under an epifluorescence microscope. (B) Quantitation of the numbers of VSV transduced GFP-expressing cells at 24 hours post infection (MOI 0.1). Data show the average of three independent experiments.
Figure 4B:
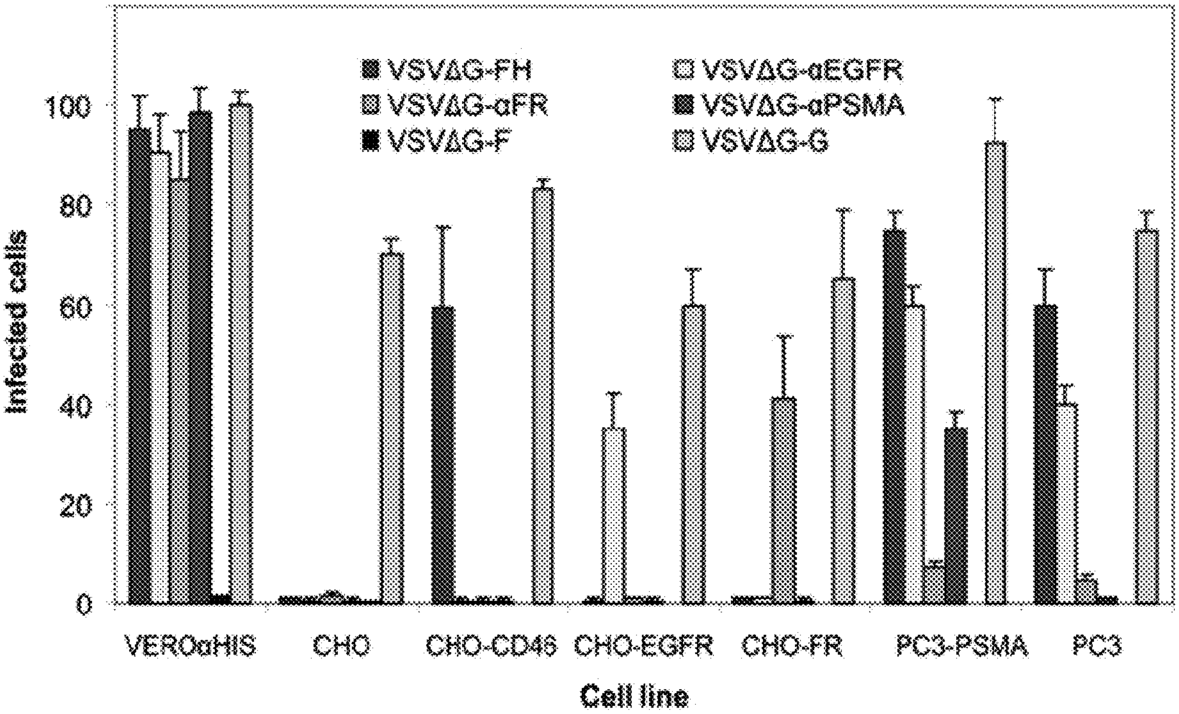
Figure 5:
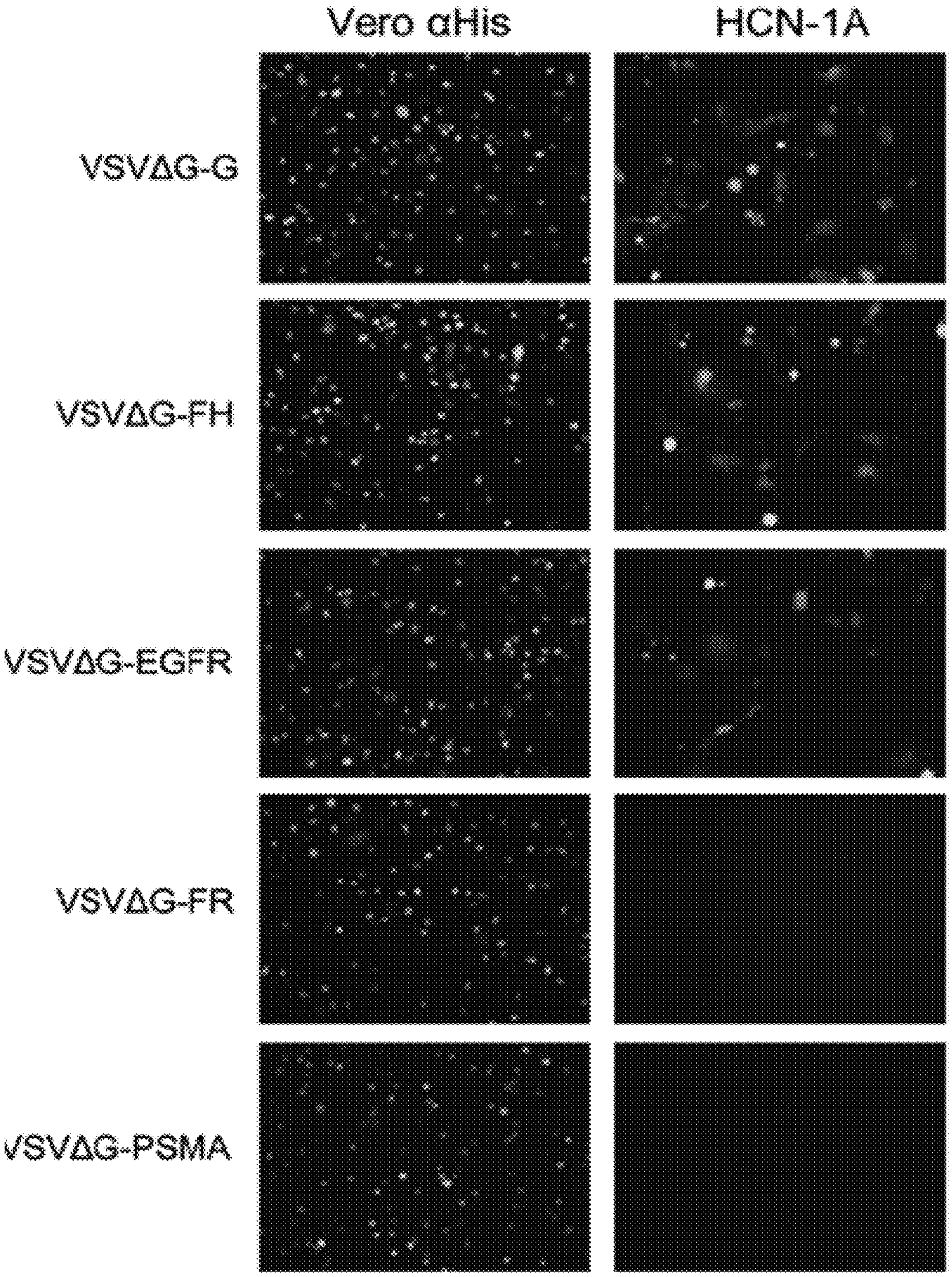
FIG. 5. Human neuronal cells were not transduced by αFR or αPSMA-retargeted VSVΔG pseudotypes (MOI 1.0). Representative photographs of GFP-expressing cells taken at 48 hours post transduction under an epifluorescence microscope (100× magnification) are shown.

After confirming that VSV can be pseudotyped with MVH bearing an scFv, the next step was to determine if its infectivity can indeed be retargeted to cells expressing the corresponding receptor. To test the specificity of VSV pseudotypes, virus infection was performed on an array of CHO cells expressing the specific receptors. As shown in FIG. 4A, virus entry and infection, as shown by the presence of GFP expression, were restricted to receptor-positive cells, and not in receptor-negative cells, for each of the respective retargeted VSV vectors. MV-H-scFv contained two point mutations at residues 481 and 533, rendering them unable to interact with MV natural receptors, CD46 and SLAM. Therefore, VSVΔGαEGFR, VSVΔG-αFR, and VSVΔG-αPSMA were not able to infect CHO-CD46 or CHO-SLAM cells. The numbers of GFP-positive cells were counted, demonstrating the specificity of these pseudotyped vectors (FIG. 4B). To evaluate the tropism of the VSV vectors in neurons, human cortical neuronal cells HCN-1A were transduced with VSVΔG-G or the VSVΔG-FH-retargeted vectors. These CD46, EGFR-positive human HCN-1A cells were transduced by VSVΔG-G, VSVΔG-FH, and VSVΔGαEGFR, but not by αFR- or PSMA-specific vectors (FIG. 5).

Specificity of Retargeted VSV Pseudotypes is Conserved In Vivo

Figure 6:
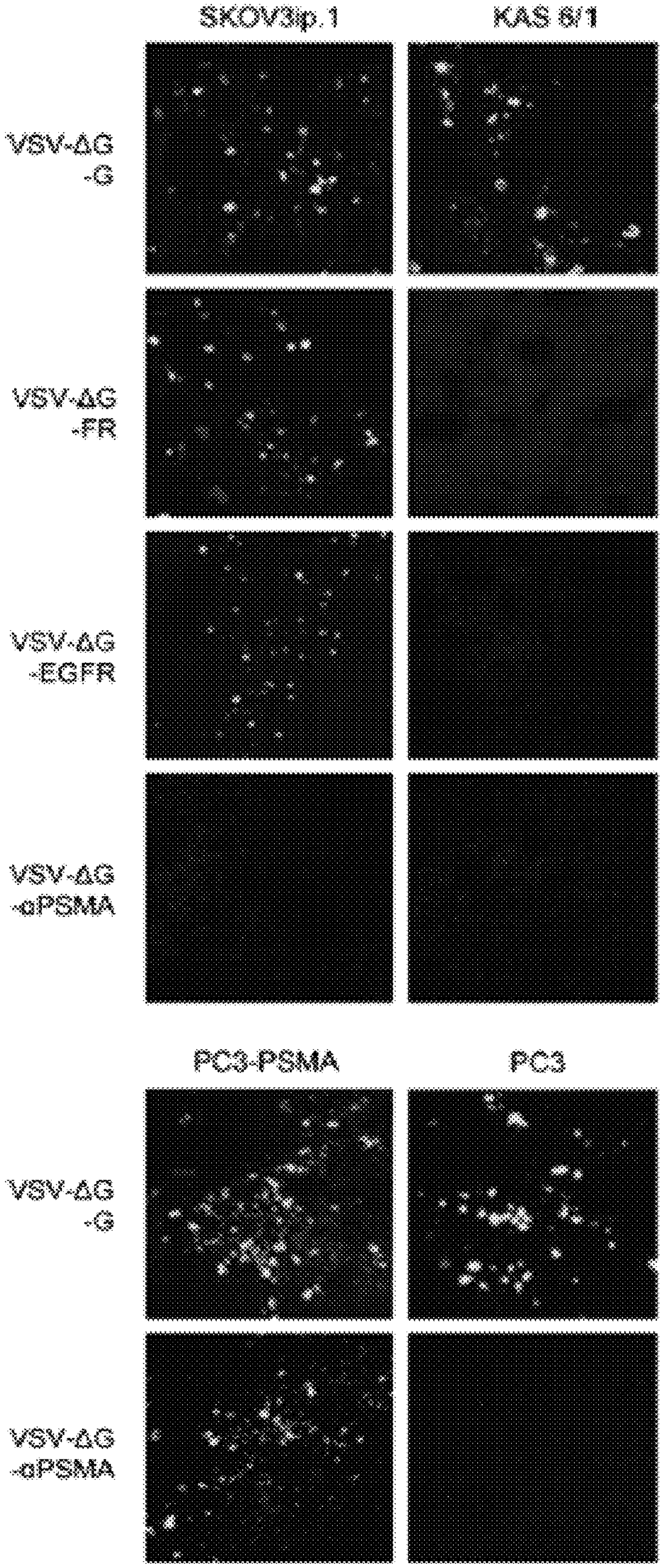
FIG. 6. Specificity of retargeted VSV pseudotypes was retained in vivo. Subcutaneous SKOV3.ip.1, KAS 6/1, PC3, or PC3-PSMA tumors were injected intratumorally with one dose of $10^6$ retargeted VSV vectors. Tumors were harvested 48 hours later, and GFP signals were detected using a fluorescence microscope. Representative images are shown (100× magnification).

After confirming that the retargeted VSV vectors specifically infected receptor-positive cells, the following was performed to determine if the same specificity is conserved when these viruses are injected in mice. Human tumor cell lines, KAS 6/1 (EGFR-, αFR-, and PSMA-negative cells), SKOV3ip.1 (EGFR- and αFR-positive cells), PC3 (PSMA-negative cells), and PC3-PSMA cells were injected subcutaneously in the flanks of either SCID or athymic mice. Once the tumors reached 0.5 cm in diameter, $10^6$ infectious viruses were injected intratumorally. The tumors were harvested 2 days later for analysis. As shown in FIG. 6, there was robust GFP expression in the receptor-positive tumor, but not in receptor-negative tumors. Hence, this confirmed that the corresponding retargeted VSV vectors were stable and maintained their tropism in vivo and could efficiently infect receptor-positive tumors (FIG. 6).

Figure 7:
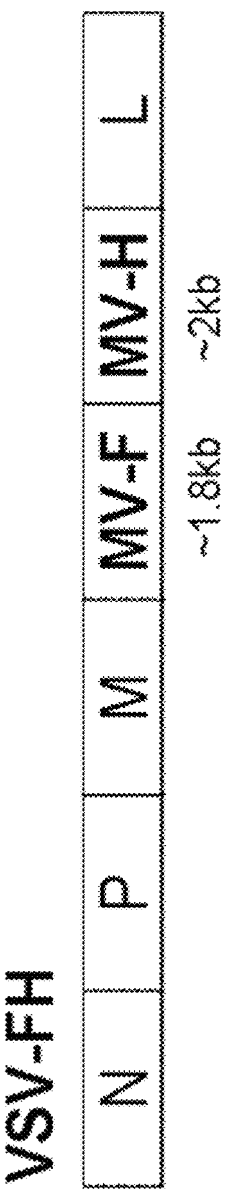
FIG. 7 is a schematic of a possible genomic arrangement of vesicular stomatitis virus/measles virus hybrids.

Example 2—Producing Replication-Competent Vesicular Stomatitis Virus Retargeted Using Measles Virus Envelope Glycoproteins To produce replication-competent VSV-FH viruses, a plasmid containing VSV (Indiana strain) full length genome was digested with restriction enzymes to remove VSV-G nucleic acid. Then, MV-F nucleic acid and MV-H nucleic acid (each one was preceded by a VSV intergenic region like the rest of VSV genes) were cloned between VSV-M and VSV-L genes (FIG. 7), and the viruses were rescued using techniques similar to those described elsewhere (Schnell et al., *PNAS,* 93:11359-11365 (1996), Obuchi et al., *J. Virol.,*

77(16):8843-56 (2003)); Goel et al., *Blood,* 110(7):2342-50 (2007)); and Kelly et al., *J. Virol.,* 84(3):1550-62 (2010)).

The viruses were used to infect Vero cells, which express measles virus receptor CD46. VSV-FH was replicated and used to produce new infectious virions by itself.

Figure 8:
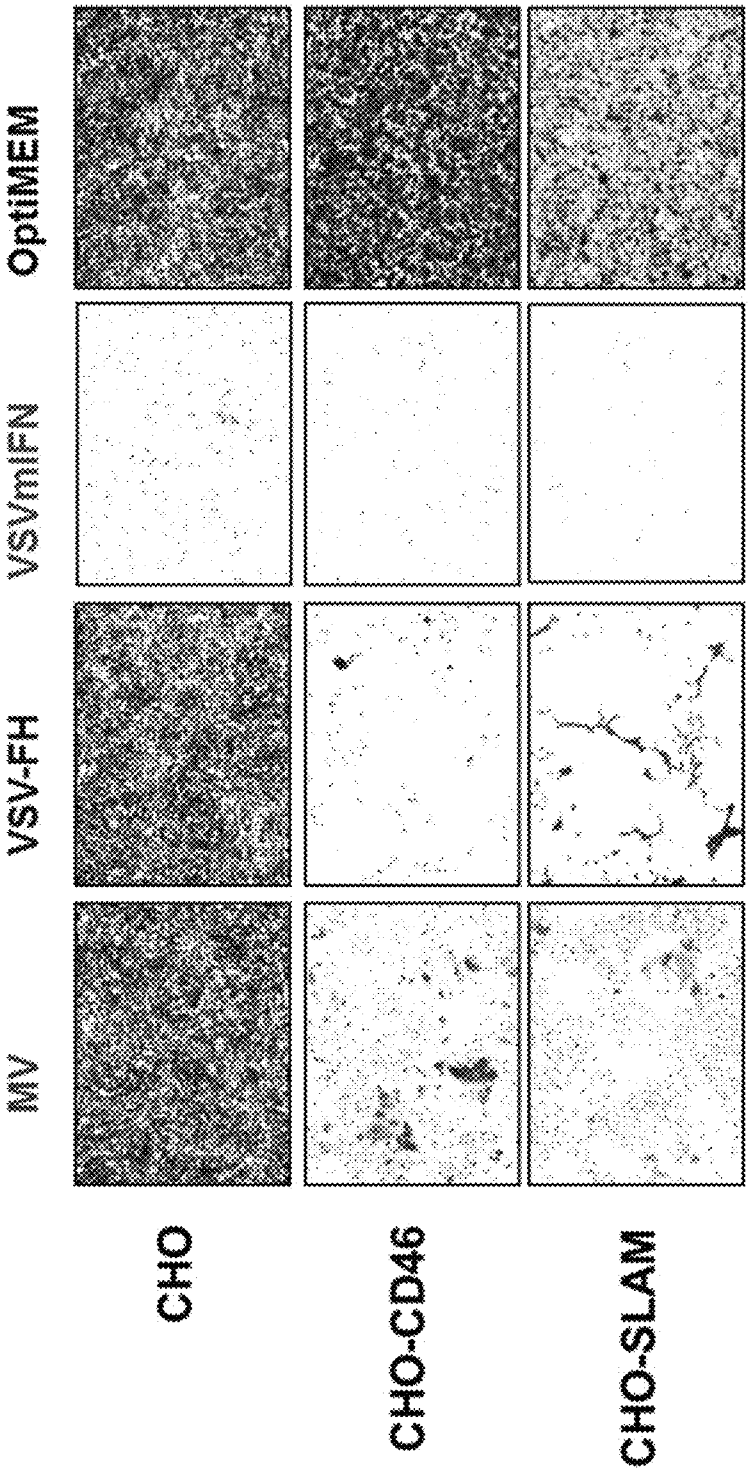
FIG. 8. CHO cells were infected with MV, replication-competent VSV-FH, or VSVmIFN at a MOI of 1. 72 hours post-infection cells were fixed and stained using the crystal violet assay.

In vitro analysis of VSV-FH revealed that the tropism of this new oncolytic virus was restricted to those cells expressing the MV natural receptors: CD46 or SLAM (FIG. 8). Since parental VSV and VSV-FH have the same replication machinery, this new VSV-FH hybrid virus presented a robust production and release of infectious particles into the extracellular media. Moreover, due to the expression of MV glycoproteins, VSV-FH can trigger the fusion of neighbor cells to form syncytia, thereby significantly increasing intracellular viral spread.

Figure 9:
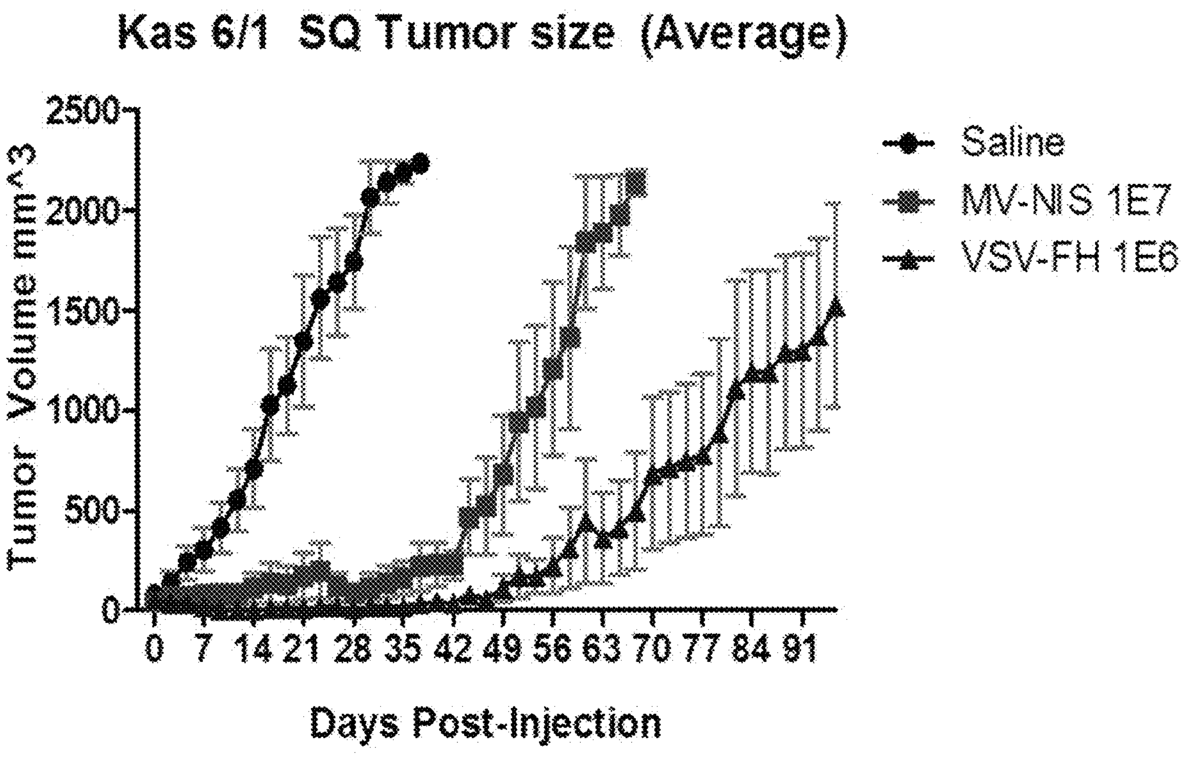
FIG. 9. Kas 6/1 tumors were subcutaneously implanted in the right flank of SCID mice. When tumors reached 0.5 cm volume, MV-NIS or replication-competent VSV-FH at the indicated doses were intravenously injected. Tumor volumes were measured at different days post-injection.

In vivo, a single intravenous dose of $1\times10^6$ $TCID_{50}$ of replication-competent VSV-FH resulted in a significant reduction in the volumes of subcutaneous human myeloma tumors compared to a ten times higher dose ($1\times10^7$ $TCID_{50}$) of MV-NIS (FIG. 9). MV-NIS is a measles virus designed to express a human sodium iodide symporter polypeptide. The median survival also was higher (80 days) for mice treated with replication-competent VSV-FH than those treated with MV-NIS (60 days, $p<0.05$) or saline solution (28 days, $p=0.005$).

Histological analysis of tumors treated with replication-competent VSV-FH revealed a high percentage of VSV-positive tumors cells. The presence of infectious VSV-FH particles indicates that the virus was able to replicate and spread within the tumor. These results demonstrate that VSV-FH viruses have effective replication and spread kinetics and in vivo antitumor activity compared to MV-NIS. In addition, replication-competent VSV-FH is capable of being further retargeted to display single-chain antibodies to achieve receptor mediated virus entry and spread, thereby increasing its tumor selectivity and eliminating concerns with potential neurotoxicity such as the potential neurotoxicity associated with experimental inoculation of VSV in rodents. Replication-competent VSV-FH viruses also have the ability to overcome the antiviral effects of host immunity better than wild-type VSV due to the fusogenic properties of the replication-competent VSV-FH viruses.

Example 3—Attenuation of Oncolytic Vesicular Stomatitis Virus Through Tropism Engineering

Cell Culture

All the cells were cultured at 37° C. in 5% $CO_2$ atmosphere. Vero, Baby Hamster Kidney (BHK), SW579 (squamous cell carcinoma from the thyroid), and LoVo (colorectal adenocarcinoma) cells were purchased from the American Type Culture Collection (ATCC). Human Multiple Myeloma cell line KAS 6/1 was obtained from Dr. Diane Jelinek (Mayo Clinic, Rochester, Minn.), KAS 6/1 F/G-Luc cells were generated by transduction using lentiviral vectors expressing Gaussia and Firefly luciferase proteins as described elsewhere (Liu et al., *Mol. Ther.,* 18:1155-1164 (2010)); RPMI 8226 were obtained from Dr. John Lust (Mayo Clinic, Rochester, Minn.); and MM1 and JJN3 cells were obtained from Dr. Rafael Fonseca (Mayo Clinic, Rochester, Minn.). Human ovarian cancer cells SKOV3.ip1 were obtained from Dr. Ellen Vitetta (University of Texas Southwestern Medical Center). Chinese Hamster Ovary (CHO) cells and CHO cells expressing CD46 (CHO-CD46) or SLAM (CHO-SLAM) are described elsewhere (Nakamura et al., *Nat. Biotechnol.,* 22:331-336 (2004)).

Cloning and Rescue of VSV-FH

Figures 10A, 10B:
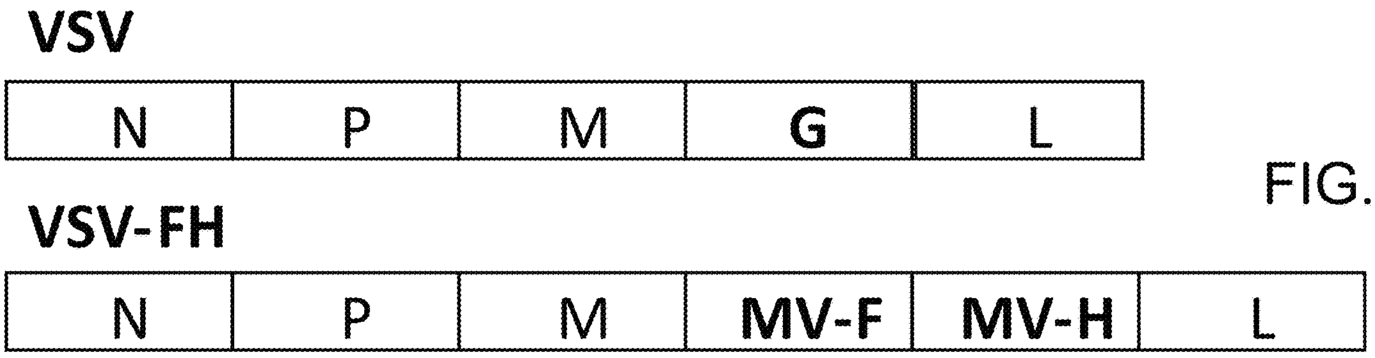
FIGS. 10A-10B.

MV-F was subcloned into Zero Blunt Topo vector (Invitrogen, Carlsbad, Calif., USA), using the plasmid pCGF as template for PCR and the primers set forth in FIG. 10B. Then MV-F was digested with NotI and cloned into a plasmid containing VSV-mIFN full-genome sequence (obtained from Dr. Glen Barber, University of Miami School of Medicine, Miami, Fla.). To remove VSV-G and mIFN from this construct, the plasmid was digested with NotI and XhoI, and the ends were blunted by using the Quick Blunting Kit (New England Biolabs, Ipswich, Mass., USA). The resulting plasmid is VSVDG-F. Then, MV-H was subcloned into Zero Blunt Topo Vector by PCR amplification use primers set forth in FIG. 10B. The MV-H gene was then excised using SphI and cloned into pVSVDG-F. Fully replication-competent VSV-FH was obtained using the plasmid pVSVDG-FH using the VSV rescue system described elsewhere (Lawson et al., *Proc. Natl. Acad. Sci. USA,* 92:4477-4481 (1995)).

To produce large amounts of VSV-FH, $2\times10^7$ Vero cells in 150 $mm^2$ dishes were infected with VSVFH at a MOI of 0.00001 in 13 mL of opti-MEM (Invitrogen). Supernatant was harvested at three days post-infection, and cell debris was spun down at 3000 rpm. To concentrate the virus, supernatants were concentrated using Amicon Ultra-15 Centrifugal Filters (Millipore, Billerica, Mass., USA).

Western Blots $1.5\times10^5$ $TCID_{50}$ particles were loaded per lane and fractionated PAGE in 10% Tris-HCl Criterion precast gel (Bio-Rad, Hercules, Calif.) and transferred to a polyvinylidene difluoride membrane (Bio-Rad). Membranes were blocked (5% nonfat milk in Tris-buffered saline (TBS)-Tween) and incubated with primary antibodies (monoclonal mouse αMV-N (Abcam, Cambridge, Mass.), polyclonal rabbit αMV-H and αMV-F, and polyclonal αVSV structural proteins (Hadac et al., *Virology,* 329:217-225 (2004); Jenks et al., *Hum. Gene Ther.,* 21:451-462 (2010)).

After five washes with TBS-Tween, membranes were incubated with peroxidase-conjugated secondary antibody and washed five times with TBS-tween. Signals were then developed using Pierce ECL western blotting substrate kit (Thermo Scientific, Waltham, Mass.).

Infectious Viral Particles Production $1\times10^6$ Vero cells per well of a 6-well plate were infected with MVG (MOI of 0.1), VSVFH (MOI of 0.00001), or VSV-mIFN (MOI of 0.00001) for 3 hours in 1 mL of opti-MEM. Then inoculum was removed and replaced with 2 mL of DMEM 5% FBS (v/v). At the indicated times post-infection, supernatant was recovered, cell debris were removed by centrifugation (3000 rpm for 5 minutes), and the sample stored at −80° C. Cells were washed once with opti-MEM, resuspended in 2 mL of media, scrapped from the plate, and stored at −80° C. Frozen cells and supernatant were freeze-thawed once, and the amount of infectious particles per mL was tittered in Vero-αHIS cells as described elsewhere (Hadac et al., *Virology,* 329:217-225 (2004)).

Cell Viability Assays

SW579, SKOV3.ip1, and LoVo cells (14,000 cells per well) were seeded in a 96-well plate and infected the next day with the indicated viruses at MOI of 1, 0.1, and 0.01 diluted in 50 μL of opti-MEM. U266, MM1, RPMI 8226, JJN3, and KAS 6/1 ($5\times10^5$ cells per well) were infected for three hours with the indicated viruses at MOIs of 1, 0.1 and 0.01, and then the media were removed and replaced with 100 μL of growing media. At 3 days post-infection, cell viability was measured using the CellTiter 96 Aqueous Assay (Promega, Fitchburg, Wis., USA), following the manufacturer recommendations.

In Vivo Experiments

VSV-FH Safety

C57bl/6 IFN/CD46 positive 4-5 weeks old mice were injected intravenously with $1\times10^7$ $TCID^{50}$ units of the VSV-FH (n=7), VSV-M51-NIS (n=6), or VSV-GFP (n=6), or 100 μL of opti MEM (n=4). Body weight was measured every day for the first 12 days post-injection. Mice were sacrificed when neurotoxicity symptoms were observed (e.g., limb paralysis, tremors, lethargic behavior, low-weight, etc.). At day 30 post-injection, blood was extracted from surviving mice and assayed for the presence of αMV and a VSV antibodies by enzyme-linked immunoassay (ELISA) and the presence of neutralizing antibodies against MV or VSV by plaque-reduction neutralization as described elsewhere (Ayala-Breton et al., *Hum. Gene Ther.,* 23:484-491 (2012)).

VSV-FH Efficacy Against Subcutaneous Plasmacytomas 4-6 weeks old ICR SCID mice were purchased from Taconic (Germantown, N.Y.). One day before implantation of xenografts, mice were whole body irradiated (2 Gy). The next day, $2\times10^6$ KAS 6/1 cells were implanted subcutaneously in the right flank of the mice. When tumors reached a volume of 50 $mm^3$, $1\times10^7$ $TCID_{50}$ units of MV-NIS (n=6) or VSV-M51-NIS (n=8), $1\times10^6$ $TCID^{50}$ units of VSV-FH (n=7), or 100 μL of saline solution (n=8) were injected through tail vein injection. Tumor volume was measured three times per week, and mice were sacrificed when the tumor reached a volume equal to or larger than 2000 $mm^3$ or presented paralysis, head drop, lethargy, or weight loss higher than 20%.

VSV-FH Efficacy Against KAS 6/1 Disseminated Model 4-6 weeks old ICR SCID mice (Taconic) were injected with $1\times10^7$ lentivirus-transduced KAS 6/1 cells expressing Firefly and Gaussia Luciferase (Liu et al., *Mol. Ther.,* 18:1155-1164 (2010)). Tumor burden was monitored by quantifying the presence of Gaussia luciferase in blood using a Top Count NXT Scintillation and Luminescence Counter (Perkin Elmer, Waltham, Mass., U. S) in a black 96-well plate at wavelength of 470 nm and the Biolux Gaussia luciferase assay kit (New England Biolabs) following manufacturer instructions. Mice were treated when most of the animals presented relative lights units (RLU) around 30,000/5 μL of blood. Groups were intravenously injected with 3 doses of $1\times10^6$ $TCID_{50}$ units in 100 μL of opti-MEM of the indicated viruses or vehicle only (n=10 per group) at days 31, 38, and 41 post-implantation. Mice were monitored daily and euthanized when presented paralysis, head drop, lethargy, or weight loss higher than 20%.

Viral Spreading in Solid Tumors

KAS 6/1 subcutaneous tumors were implanted as described herein. When the tumor reached a volume of 50 $mm^3$, mice were intravenously injected with $1\times10^7$ $TCID_{50}$ units of VSV-FH, VSV-M51-NIS, or MV-NIS, or with 100 μL of opti-MEM. At days 3 and 6 post-injection, mice were sacrificed, and tumors were removed. Half of the tumor was frozen in Optimal Cutting medium (OCT) and cut in 0.2 m slices. These sections were fixed with acetone and stained with αVSV polyclonal antibody or αMV-N monoclonal antibody. Alexa-conjugated anti-rabbit or anti-mouse were used as secondary antibodies (Life Technologies, NY, USA). Nuclei were stained using Hoechst 33342 (Life Technologies). A small part of the tumor (approximately 1/10th) was homogenized with the help of a disposable homogenization pestle in 500 μL of opti-MEM and freeze-thawed three times to release the intracellular infectious particles. Viral titers were determined in Vero-αHIS cells as described elsewhere (Hadac et al., *Virology,* 329:217-225 (2004)). Viral titers were normalized according to the weight of the tumor section and reported as $TCID_{50}$ units per gram of tumor.

Interferon α and β Quantitation $5\times10^5$ cells were infected with either VSV-FH or VSV-M51-NIS at a MOI of 1. 48 hours post-infection, the supernatant was harvested. Secreted IFNα or IFNβ was quantified using Human IFN ELISA kit (R&D Systems, Minneapolis, Minn., USA) following manufacturer instructions.

Results

VSV-FH has the Same Tropism as MV but Looks and Behaves Like VSV

A replication-competent VSV expressing measles F and H glycoproteins (VSV-FH) was generated to incorporate the fast replication machinery of VSV with the tumor selective tropism of MV. The G glycoprotein (1.6 Kb) at position 4 of the full-length infectious cDNA clone of VSV was removed and replaced by MV-F (1.8 Kb) and MV-H (2 Kb) at positions 4 and 5, respectively (FIG. 10). The infectious VSV-FH virus was rescued and characterized biochemically and in infection assays.

Figure 11A:
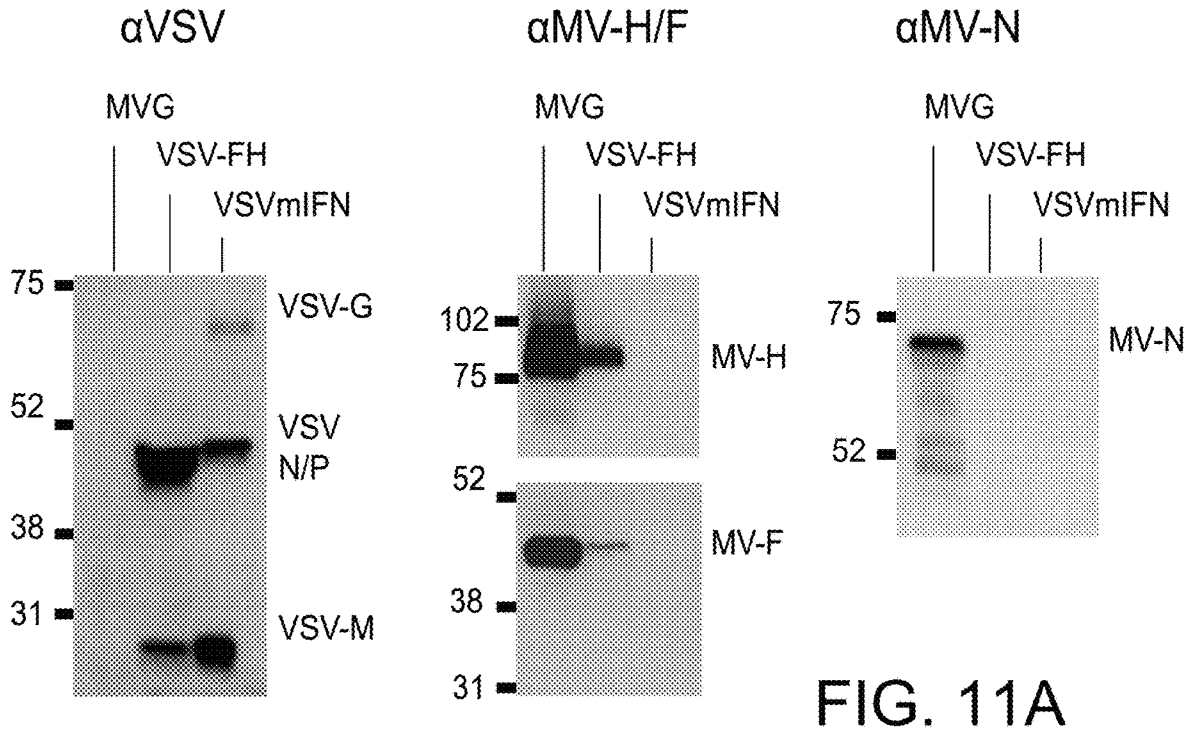
FIGS. 11A-D. Characterization of VSV-FH hybrid virus. (a) Immunoblots of purified virions using the indicated antibodies. (b) Transmission electron microscopy of purified virions. Arrows indicate the magnified area (shown below). Bar=100 nm. (c) VSV-FH is fusogenic on Vero cells. Cells were stained with crystal violet and photographed at indicated times post infection. (d) Specificity of receptor usage by VSV-FH. CHO cells were infected with the respective viruses (MOI 0.1) and stained with crystal violet 3 days post-infection.

The chimeric nature of VSV-FH was confirmed by western blot analysis using antibodies against MV nucleocapsid (N), F proteins, H proteins, or anti-VSV antisera. An equivalent amount ($10^5$; half-maximal tissue culture infective dose, $TCID_{50}$) of VSV-FH, MV expressing GFP (MVG) and VSV expressing murine IFNβ (VSV-mIFNβ) virions were loaded on the gels (FIG. 11*a*). The VSV-FH virus was a chimera of VSV and MV. Unlike VSV-mIFNβ, VSV-FH did not contain VSV-G, but MV-F and MV-H instead. VSVFH incorporated VSV N, M, phosphoprotein (P), and not MV-N.

Figure 11B:
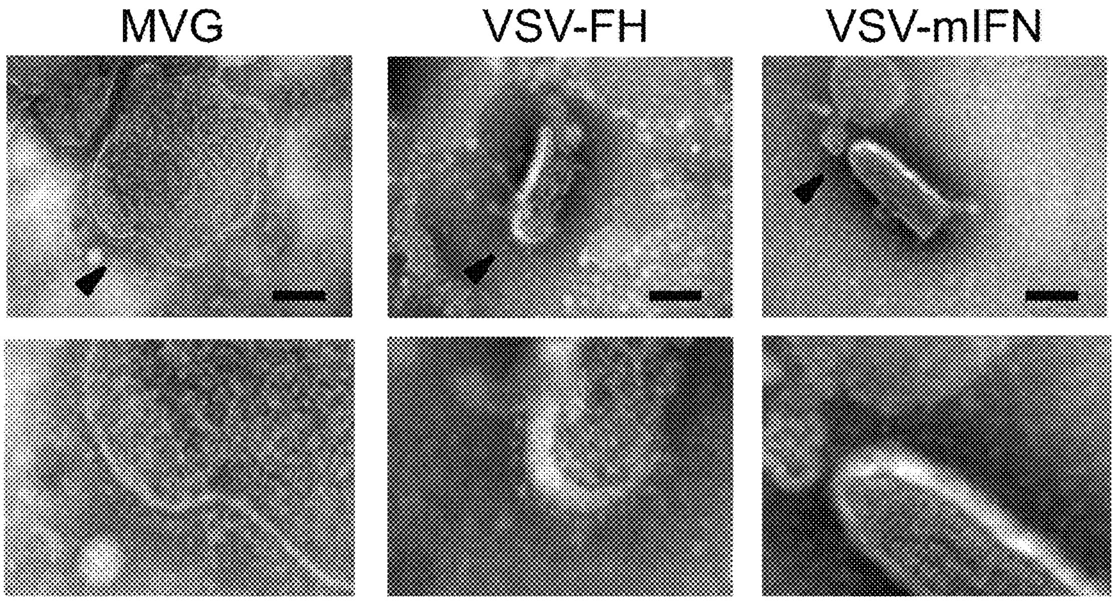

Transmission electron microscopy studies were performed to evaluate the morphology of negatively stained virions. Measles was a pleomorphic virus that contained multiple genome copies of ribonucleoprotein RNP complexes and was enveloped by a coat of F and H glycoproteins (FIG. 11*b*). In contrast, VSV was a bullet shaped virus (FIG. 11*b*). The hybrid VSV-FH was a bullet-shaped nanoparticle that was 204 nm long and 76 nm wide (average of 20 structures). From the electron micrographs, F and H glycoproteins can be seen on the VSV-FH coat. These distinctive structures were absent from the VSVmIFN 3 virions (FIG. 11*b*).

Figure 11C:
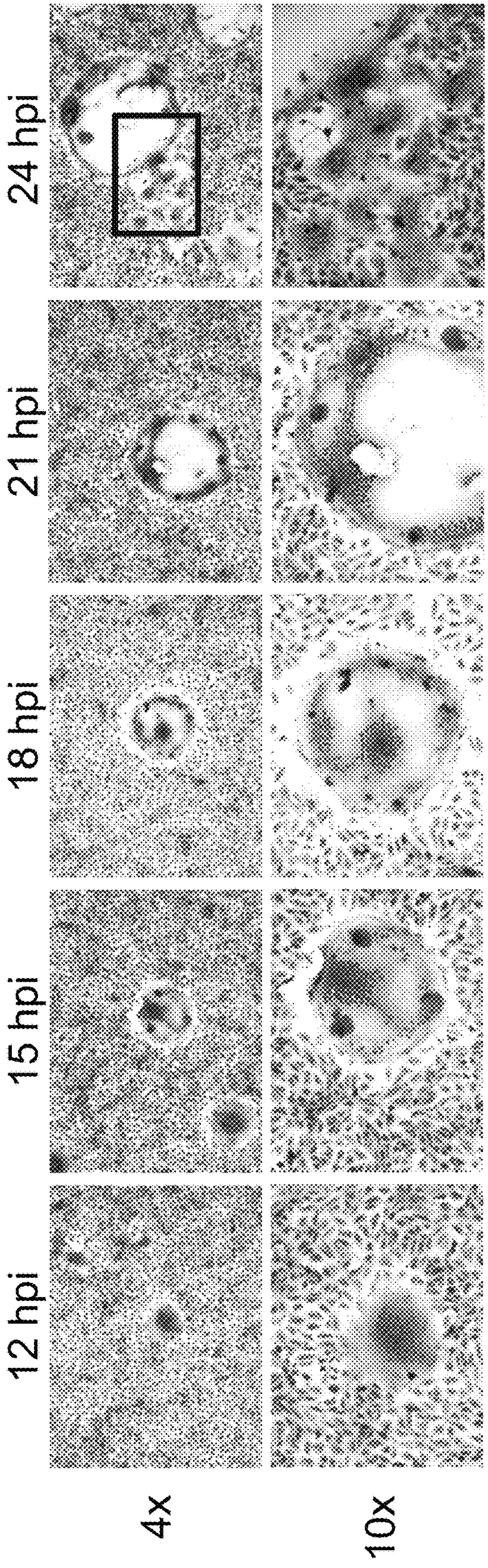
Figure 11D:
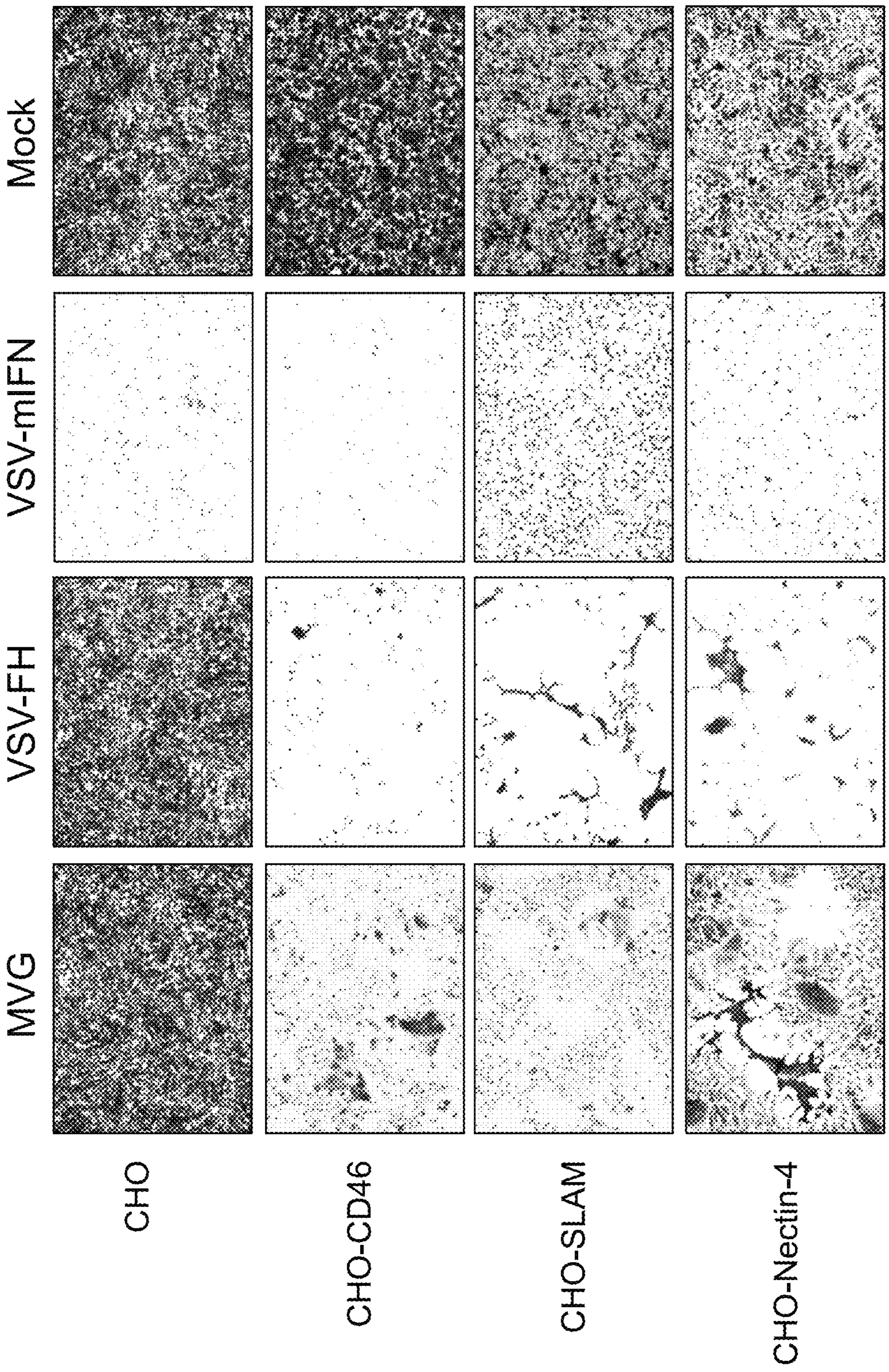

Cell infection assays revealed that VSV-FH induced rapid intercellular fusion in the monolayer (FIG. 11*c*). This cytopathic effect (CPE) of syncytial formation was characteristic of MV infection, but not of VSV, which instead caused cells to round up and lyse. Intercellular fusion of VSV-FH infected cells could be detected at 12 hours post-infection (MOI 0.001), and the numbers of infectious foci and syncytia numbers continued to grow rapidly. To assess the tropism of VSV-FH, Chinese hamster ovary cells (CHO) cells expressing MV receptors, CD46, SLAM, or Nectin-4, were infected by the viruses (FIG. 11*d*). Fusion triggering of VSV G glycoprotein was activated by low pH, but measles fusion was pH independent and was initiated upon binding of H to one of the three MV receptors (CD46, SLAM, or nectin-4) (Roche et al., *Cell. Mol. Life Sci.,* 65: 1716-1728 (2008); and Navaratnarajah et al., *Curr. Top. Microbiol. Immunol.,* 329:59-76 (2009)). MVG and VSV-FH shared a similar tropism (FIG. 11*d*). They were nonpermissive on CHO cells that lack MV receptors, but were infectious on CD46, SLAM, or Nectin-4 positive CHO cell lines. In contrast, VSV-mIFNβ was able to infect all of the four cell lines, including parental CHO via the yet to be identified VSV receptor(s). These data confirmed that the VSV-FH tropism was dictated exclusively by the measles H and F proteins incorporated on the viral coat.

VSV-MV Virus is More Potent than MV In Vitro

Figure 12A:
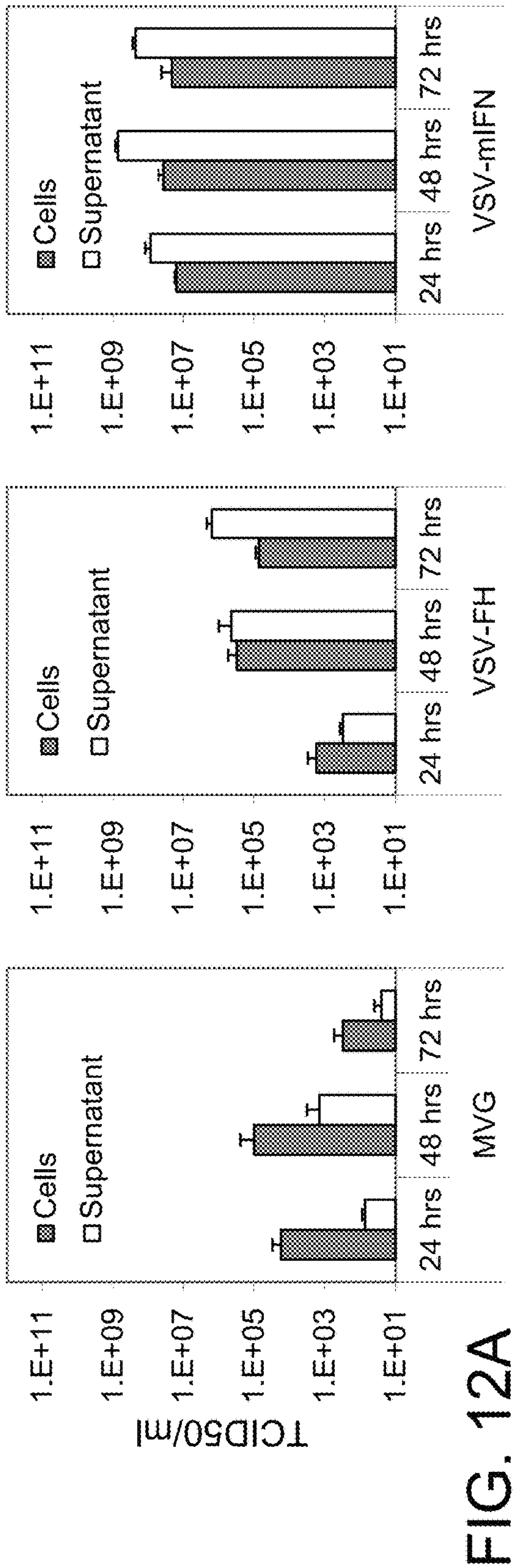
FIGS. 12A-12C. Viral replication and cytopathic effects of VSV-FH and the parental viruses. (a) Viral progeny production over time on Vero cells. Cells and supernatant were harvested at the indicated times, and the amount of infectious particles was determined by $TCID_{50}$ titrations (mean±SEM, n=3). Cytopathic effect on Vero cells after virus infection at (b) different multiplicities of infection (MOI) at 3 days post infection, and at (c) different times post-infection at indicated MOIs. Representative photographs of crystal violet stained cells are shown.

The replication of VSV-FH was compared to the replication of the parental viruses over three days. Vero producer cells were infected with MV, VSV-FH, and VSV-mIFNβ, and the amount of infectious particles in the cells or released into the supernatant was quantified by $TCID_{50}$ titration (FIG. 12). MV is a cell-associated virus, and most of the MV progeny were in the infected cells with little released into the supernatant (FIG. 12*a*). In contrast, VSV-mIFNβ released most of its virions into the supernatant. VSV-FH has an intermediate phenotype. At 24 hours post infection, most of the virions were found in the cells, but at later time points, most virions were released into the supernatant. Of note here is that Vero cells were infected by MV at MOI of 0.1, while MOI of 0.00001 was used for VSV-FH and VSV-mIFNβ. A lower MOI was used for VSV-FH and VSV-mIFNβ, otherwise their rapid replication would have resulted in complete destruction of the cell monolayer before 72 hours.

Figure 12B:
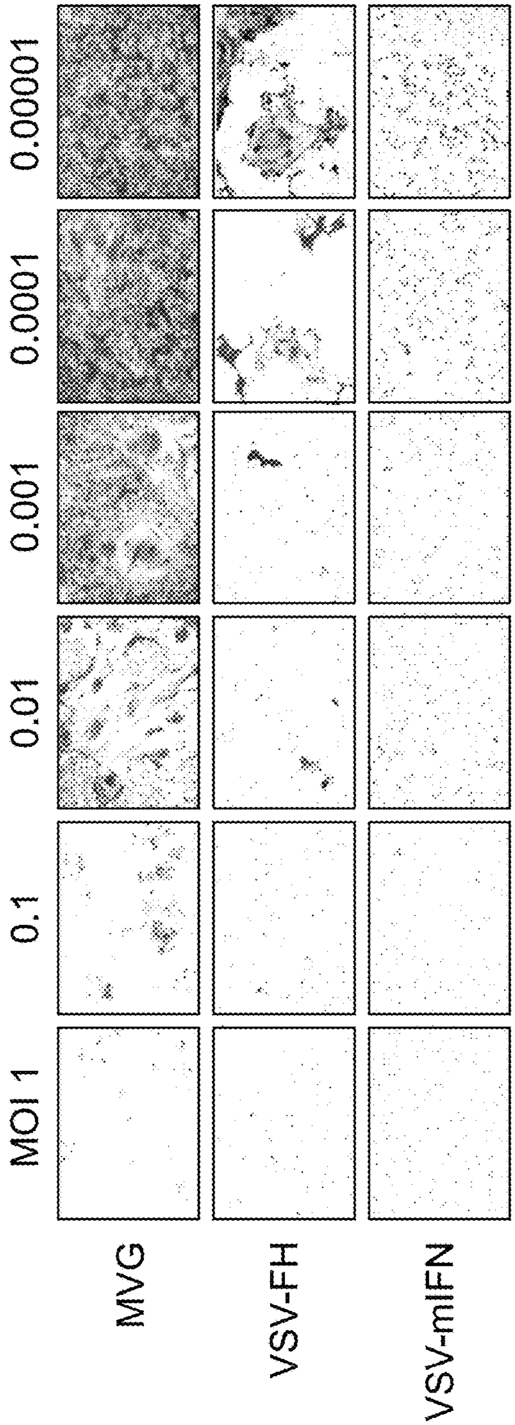
Figure 12C:
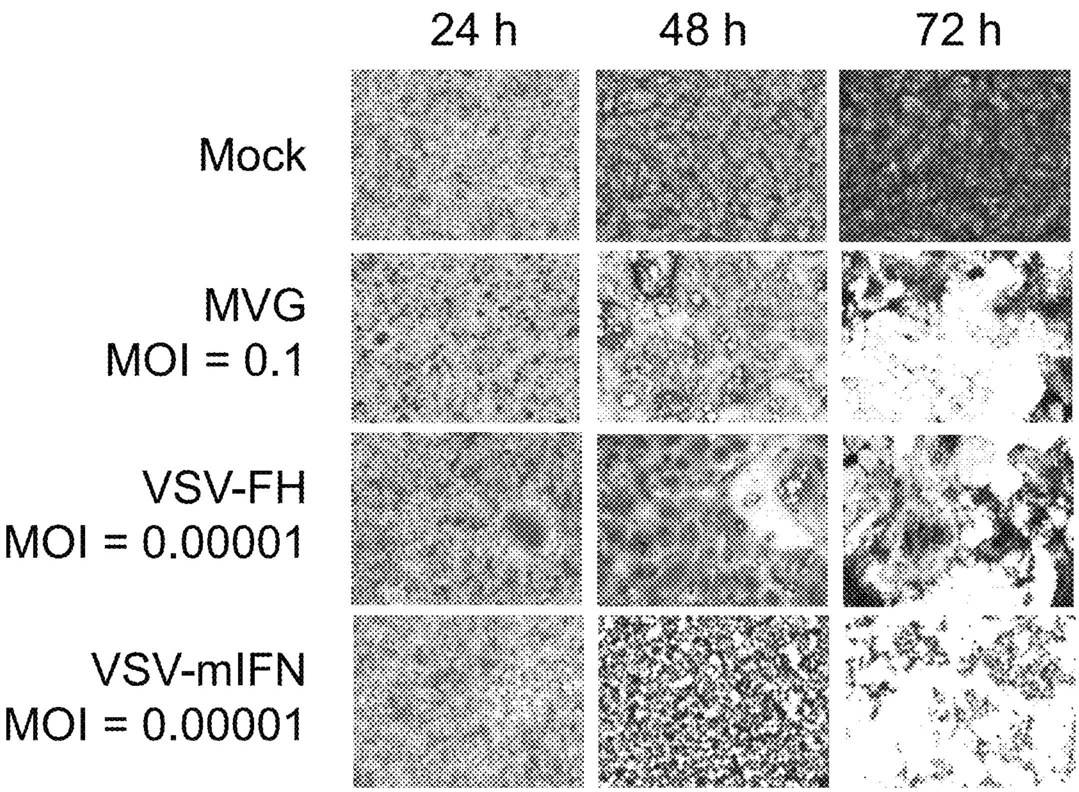
Figure 13A:
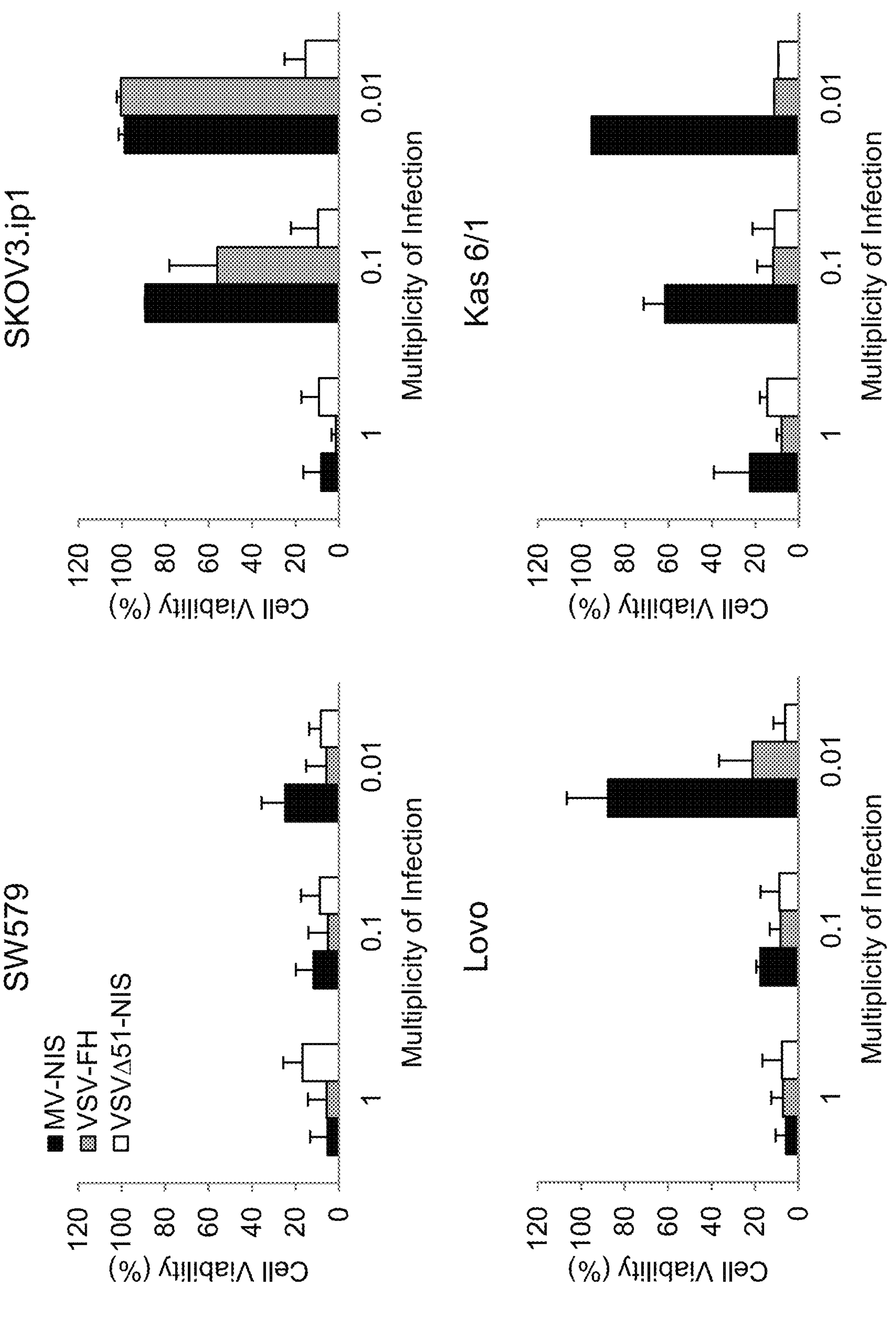
FIGS. 13A-13C. VSV-FH infection of human cells. (a) Viability of infected colorectal (LoVo), head and neck (SW579), ovarian cancer cells (SKOV3.ip1) and multiple myeloma (KAS 6/1) at 3 days postinfection. Bars represent average of three experiments (mean±SEM). (b) Viability of a panel of multiple myeloma cell lines post virus infection at 3 days. Bars represent average of three experiments (mean±SEM). (c) VSV-FH specificity on $CD138^+$ plasma cells (myeloma) and $CD138^-$ non plasma cells derived from the bone marrow of multiple myeloma patients. Representative example from two replicates is shown.
Figure 13B:
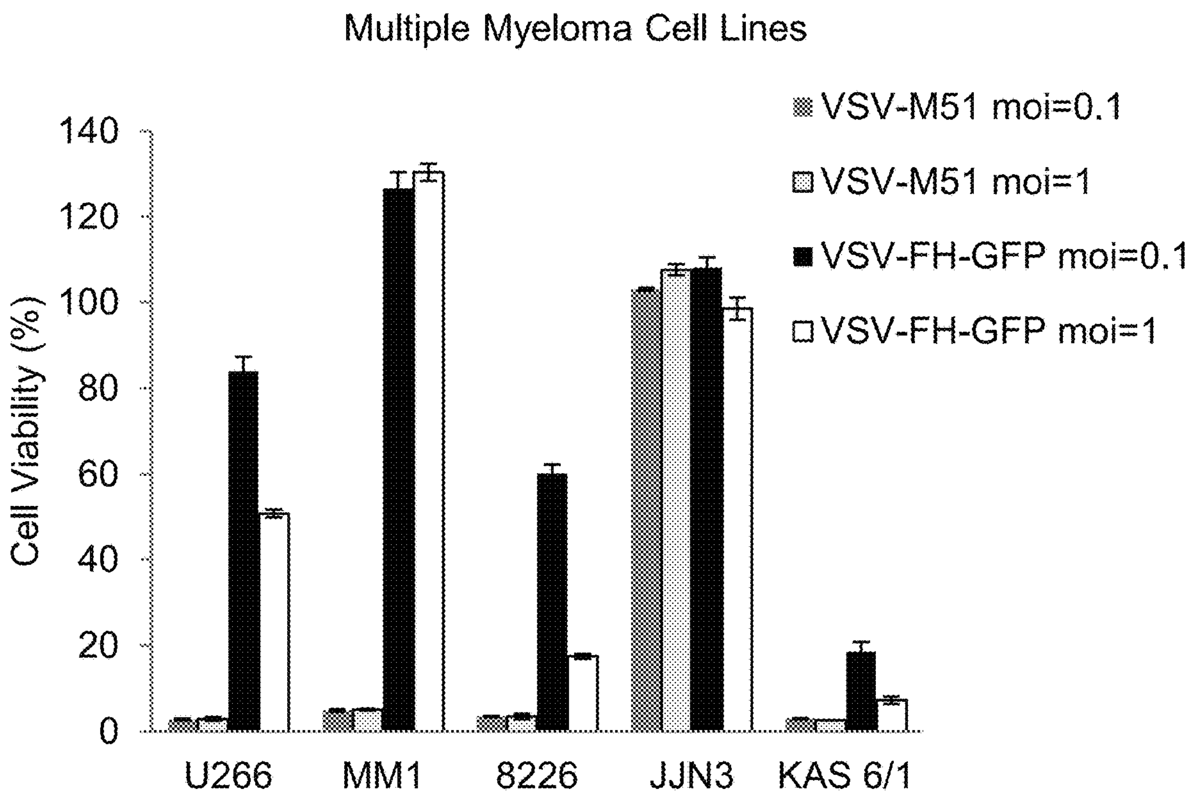

To compare the CPE of the viruses, Vero cells were infected with VSV-FH, MV, and VSV-mIFNβ with MOIs of 1.0 to 0.00001. Cells were stained with 2% crystal violet 72 hours later (FIG. 12*b*). Total destruction of the monolayer occurred at MOI of 0.1 for MVG. In contrast, the VSV-FH and VSV-mIFNβ viruses caused total destruction of the cells at 5-log lower MOI of 0.00001. The MOI required for these viruses to achieve 100% destruction of the cell monolayer at 72 hours also was examined. Comparable CPE was achieved at MOI 0.1 by MVG and MOI 0.00001 by VSV-mIFNβ or VSV-FH (FIG. 12*c*). The cytotoxic potential of VSV-FH was next evaluated in a panel of human cell lines and found to have varying degrees of potency. FIG. 13 provides data from SW579 (squamous cell carcinoma), LoVo (colon adenocarcinoma), SKOV3.ip1 (ovarian cancer), and KAS 6/1 (multiple myeloma). MV-NIS, measles expressing the human sodium iodide symporter (NIS), and VSV-M51-NIS, both previously shown to be effective against multiple myeloma, were used as the therapeutic viruses in this comparative study (Dingli et al., *Blood,* 103:1641-1646 (2004); Goel et al., *Blood,* 110:2342-2350 (2007); and Myers et al., *Clin. Pharmacol. Ther.,* 82:700-710 (2007)). At MOI of 1.0, all three viruses were potent in all cell lines tested. At low MOI of 0.01, VSV-M51-NIS killed all cell types efficiently. At low MOI of 0.01, MV-NIS was generally not as potent as either VSV-FH or VSV-M51-NIS.

Figure 13C:
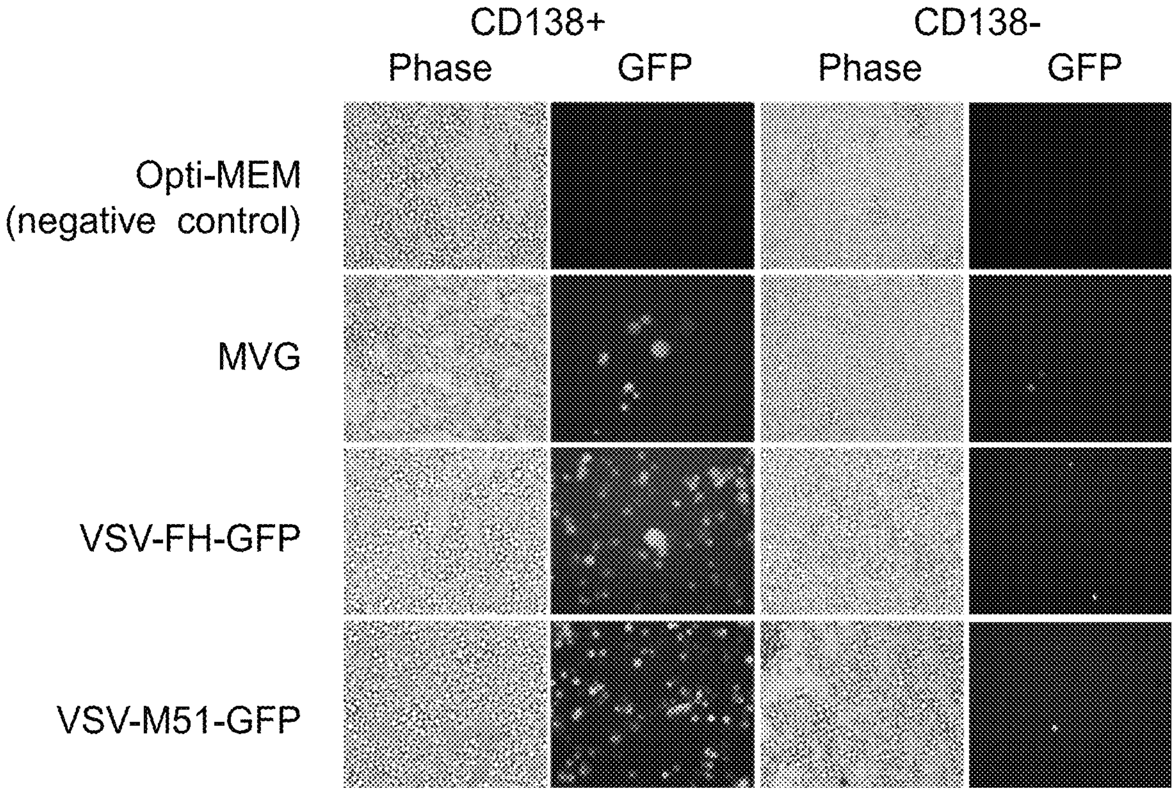

The antitumor potency of VSV-FH was further evaluated in a panel of human myeloma cell lines, U266, MM1, RPMI 8226, JJN-3, and KAS 6/1 (FIG. 13*b*) as well as cells harvested from the bone marrow aspirates of myeloma patients (FIG. 13*c*). In general, VSV-FH was less potent compared to VSVM51-GFP in vitro. In $CD138^+$ malignant plasma cells (myeloma), MV, VSV-FH, and VSV-M51-NIS exhibited good oncoselectivity for $CD138^+$ cells, but did not infect $CD138^-$ normal bone marrow stromal cells.

VSV-FH is not Neurovirulent in Mice

Figure 14A:
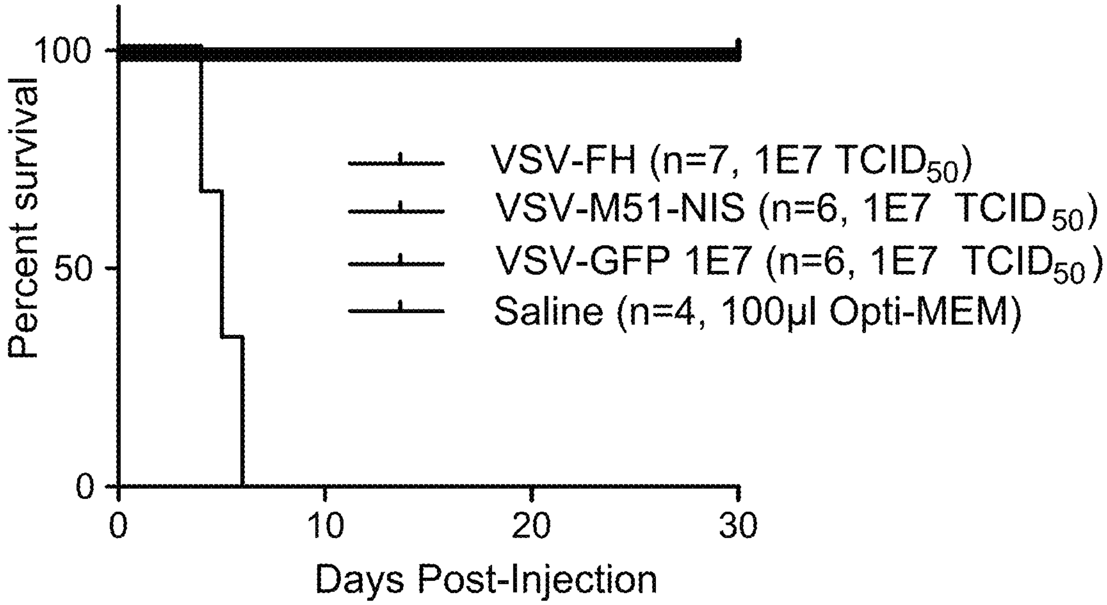
FIGS. 14A-14C. Neurovirulence study of viruses in CD46 transgenic measles susceptible mice. (a) Survival curves of mice given $10^7$ $TCID_{50}$ VSV-FH, VSV-M51-NIS, and VSV-GFP intravenously. Mice were euthanized when neurotoxic symptoms were observed. (b) Percent body weight change from baseline at the start of experiment. Mice were weighed at the indicated days post treatment. (c) Anti-VSV or anti-MV antibodies in serum of treated mice at day 30 post virus. Titers were measured by MV or VSV specific ELISA assays and by plaque reduction neutralization PRN assay.
Figure 14B:
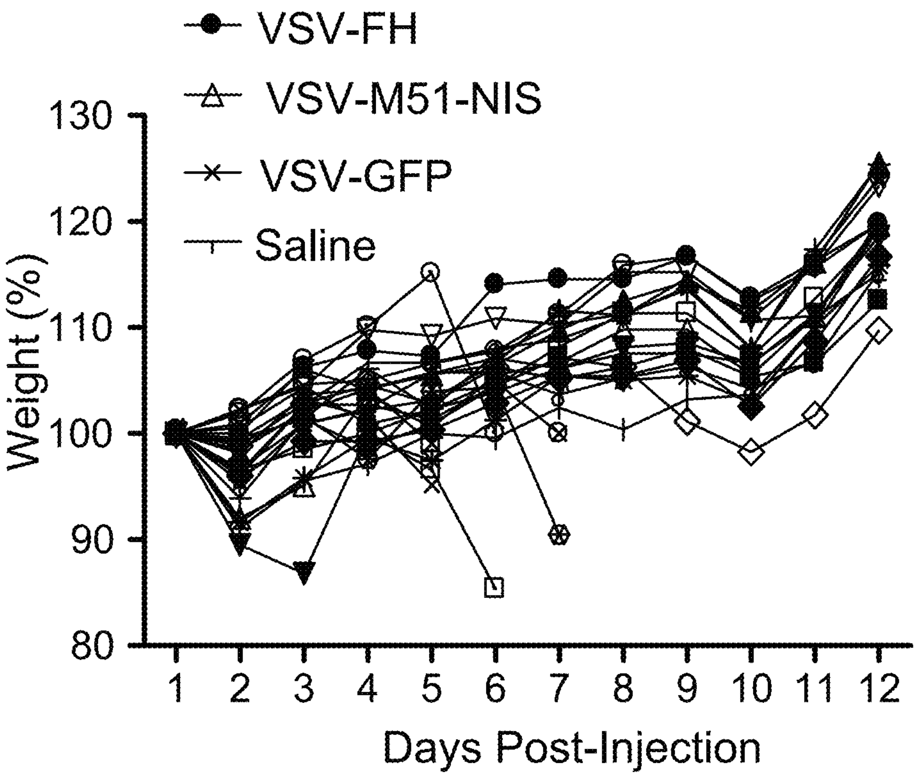

After confirming that the VSV-FH exhibited superior oncolytic activity compared to MV, its safety profile was evaluated. VSV is neurovirulent in mice (Sabin and Olitsky, *J. Exp. Med.,* 67:229-249 (1938); and Clarke et al., *J. Virol.,* 81:2056-2064 (2007)). One of the main goals with creation of this hybrid virus was to ablate the neurotoxicity associated with VSV-G interaction with neuronal cells. To test if VSV-FH was less neurotoxic than parental VSV, measles susceptible CD46 transgenic mice which express the human CD46 receptor with the same tissue specificity as in humans, were given high doses of $10^7$ $TCID_{50}$ VSV-GFP, VSV-M51-NIS, or VSV-FH intravenously. Mice given VSV-GFP (n=6) succumbed to neurotoxicity by day 6 (FIG. 14). Mice lost weight, showed clinical signs of neurotoxicity and stress (tremors, head tilt, lethargy, ungroom scruffy coat) and were euthanized. The presence of parental VSV in the brain was also confirmed by immunofluorescence using polyclonal antibodies against VSV envelope proteins. In contrast, mice given VSV-FH (n=7) or the attenuated VSV-M51-NIS (n=6) did not exhibit weight loss, continued to gain weight as the saline control mice (n=4) did, and did not show any signs of neurotoxicity (FIG. 14). Their survival curves were significantly different from VSV-GFP against VSV-M51-NIS (p=0.0007), VSV-FH (p=0.0003), or saline group (p=0.0044).

Figure 14C:
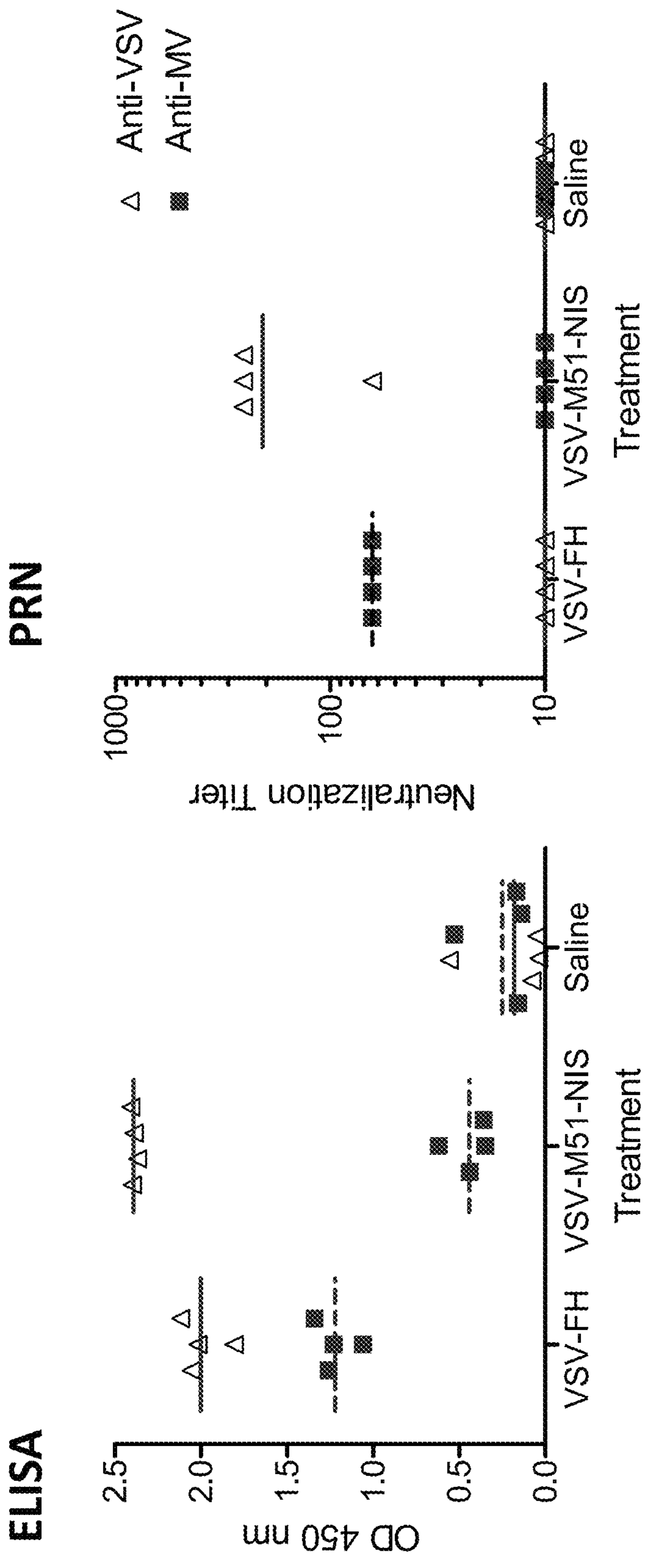

At the end of the study (30 days), mice were euthanized, and anti-VSV or anti-MV antibodies were determined by ELISA and by plaque reduction neutralization assay on Vero cells (FIG. 14*c*). Mice given VSV-FH were seropositive against MV and VSV proteins by ELISA assay (Table 1, ELISA titer) but interestingly, however, these antibodies were able to neutralize only MV but not VSV.

TABLE 1

ELISA titers (OD 450 nm) and neutralization titers of the antibodies obtained from VSV-treated mice.

| | | VSV-GFP | | MV-GFP | |
|---|---|---|---|---|---|
| | Mouse ID | Neutralized at (1/n) | OD 450 nm | Neutralized at (1/n) | OD 450 nm |
| VSVFH | 2 | <16 | 2.12 | 64 | 1.26 |
| VSVFH | 3 | <16 | 1.81 | 64 | 1.06 |
| VSVFH | 4 | <16 | 2.02 | 64 | 1.23 |
| VSVFH | 6 | <16 | 2.06 | 64 | 1.34 |
| VSVm51-NIS | 9 | 256 | 2.41 | <16 | 0.35 |
| VSVm51-NIS | 10 | 256 | 2.39 | <16 | 0.62 |
| VSVm51-NIS | 12 | 64 | 2.37 | <16 | 0.36 |
| VSVm51-NIS | 13 | 256 | 2.40 | <16 | 0.44 |
| Saline | 21 | <16 | 0.05 | <16 | 0.16 |
| Saline | 22 | <16 | 0.04 | <16 | 0.17 |
| Saline | 24 | <16 | 0.08 | <16 | 0.53 |
| Saline | 25 | <16 | 0.14 | <16 | 0.56 |
| | Positive | 64 | 3.53 | >2048 | 0.93 |
| | Negative | <16 | 0.81 | <16 | 0.21 |

VSV-FH is Highly Active Against Myeloma in Mice

Figure 15A:
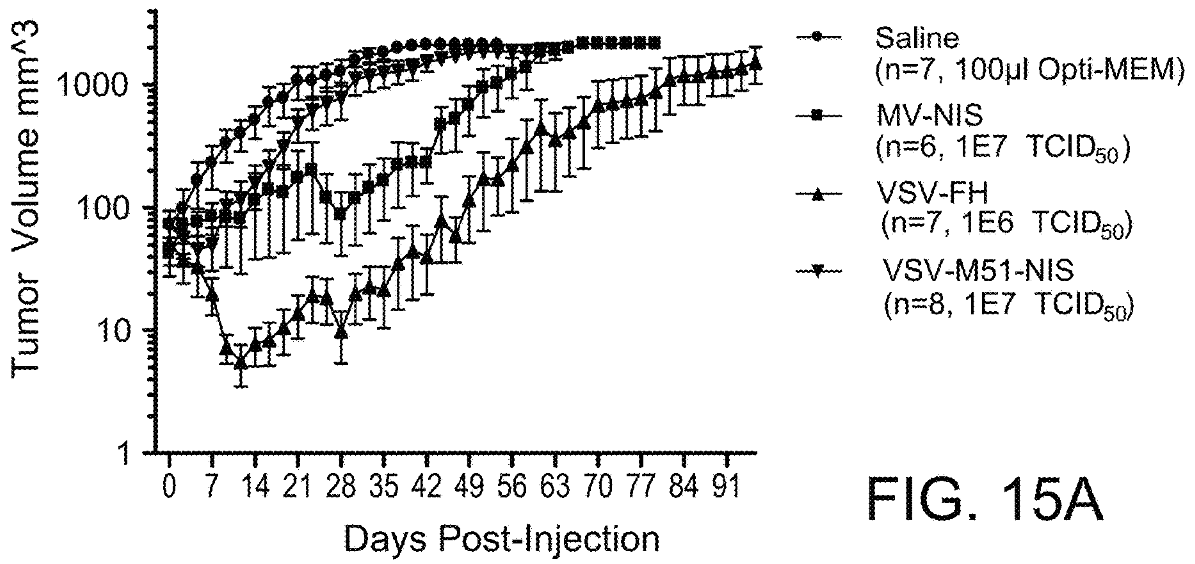
FIGS. 15A-15C. Comparative study of antitumor activities of viruses against (a, b) subcutaneous and (c) systemic human multiple myeloma KAS 6/1 tumors after intravenous delivery. (a) Volumes of subcutaneous tumors were measured and plotted on a logarithmic scale. Error bars represent SEM. Survival curves of mice with (b) subcutaneous or (c) systemic myeloma. Arrows in (c) indicates the days post-implantation when the mice were treated. Number of mice and viral dose per treatment group is shown in parentheses.
Figure 15B:
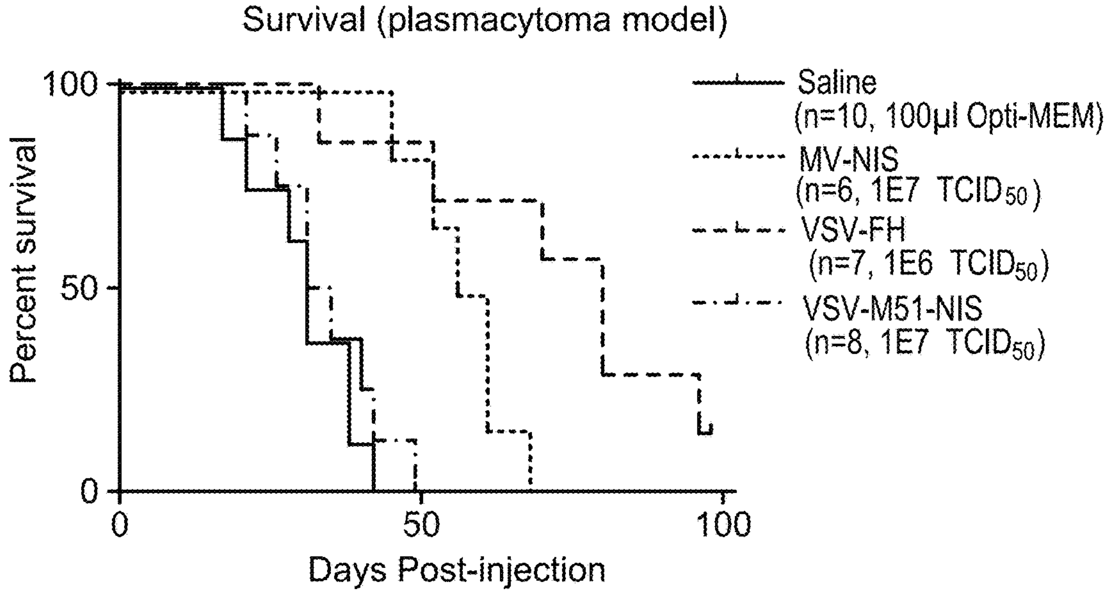

MV-NIS is being evaluated in a Phase I clinical trial in patients with relapsed or recurrent myeloma after intravenous delivery (Dingli et al., *Blood,* 103:1641-1646 (2004); and Myers et al., *Clin. Pharmacol. Ther.,* 82:700-710 (2007)). To evaluate the antitumor potential of VSVFH, SCID mice with established subcutaneous KAS 6/1 myeloma tumors (tumor diameter 0.4-0.5 cm) were given one intravenous dose of $10^7$ $TCID_{50}$ MV-NIS, $10^7$ $TCID_{50}$ VSV-M51-NIS, or 10-fold less ($10^6$ $TCID_{50}$) VSV-FH. VSV-FH was not only able to control tumor growth, but also decreased the tumor burden significantly very early post-treatment. The Kaplan Meier survival curves between VSVFH and control mice (p=0.0010) or MV-NIS (p=0.0354) or VSV-M51-NIS (p=0.0011) were significantly different (FIG. 15*b*).

Figure 15C:
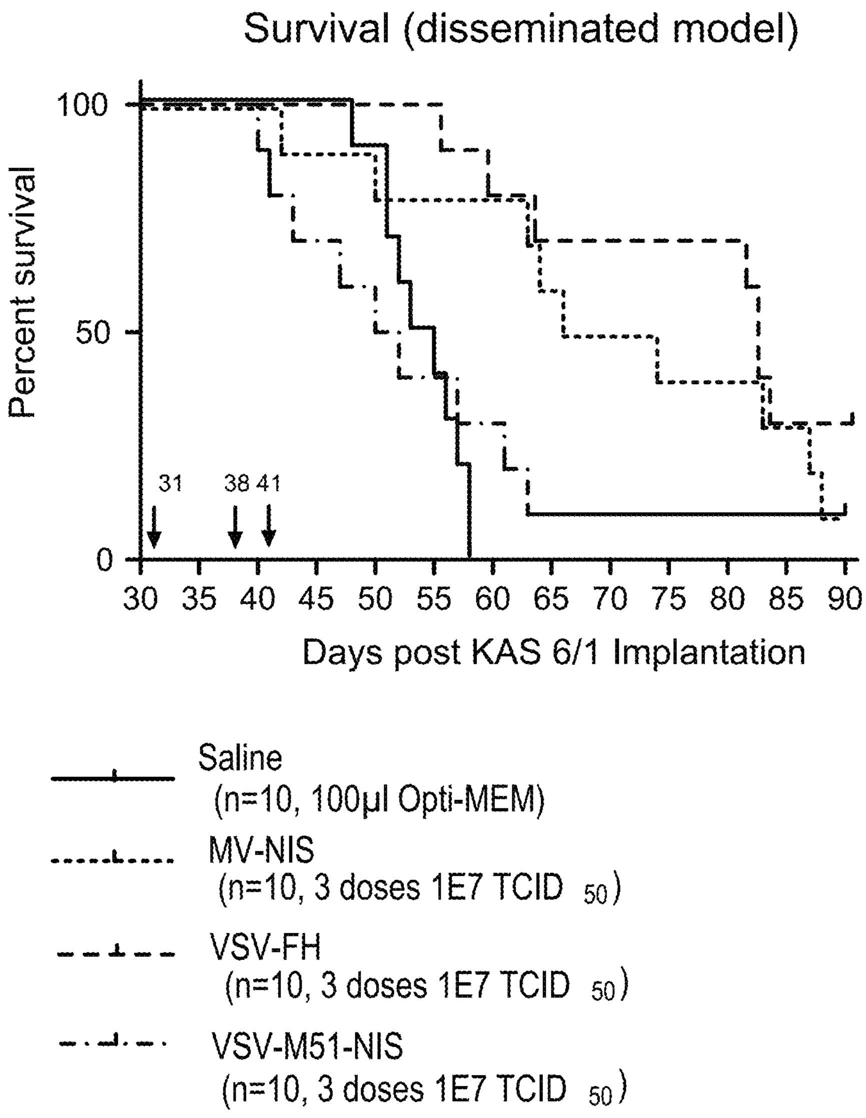

To test the efficacy of VSV-FH in a clinically relevant model, SCID mice bearing disseminated multiple myeloma, a disseminated human myeloma model characterized elsewhere (Liu et al., *Mol. Ther.,* 18:1155-1164 (2010)), were treated with three doses of $1\times10^6$ $TCID_{50}$ units of either VSV-FH, VSV-M51-NIS, or MV-NIS. Importantly, both VSV-FH and MV-NIS were able to control the disease and increased the mice survival compared to non-treated group (p=0.0138 for MV-NIS, p=0.0002 for VSV-FH). Similar to the results obtained for the subcutaneous KAS 6/1 tumors, the survival of mice treated with VSV-M51-NIS was not different from the untreated group (p=0.5424) (FIG. 15*c*).

Figure 16A:
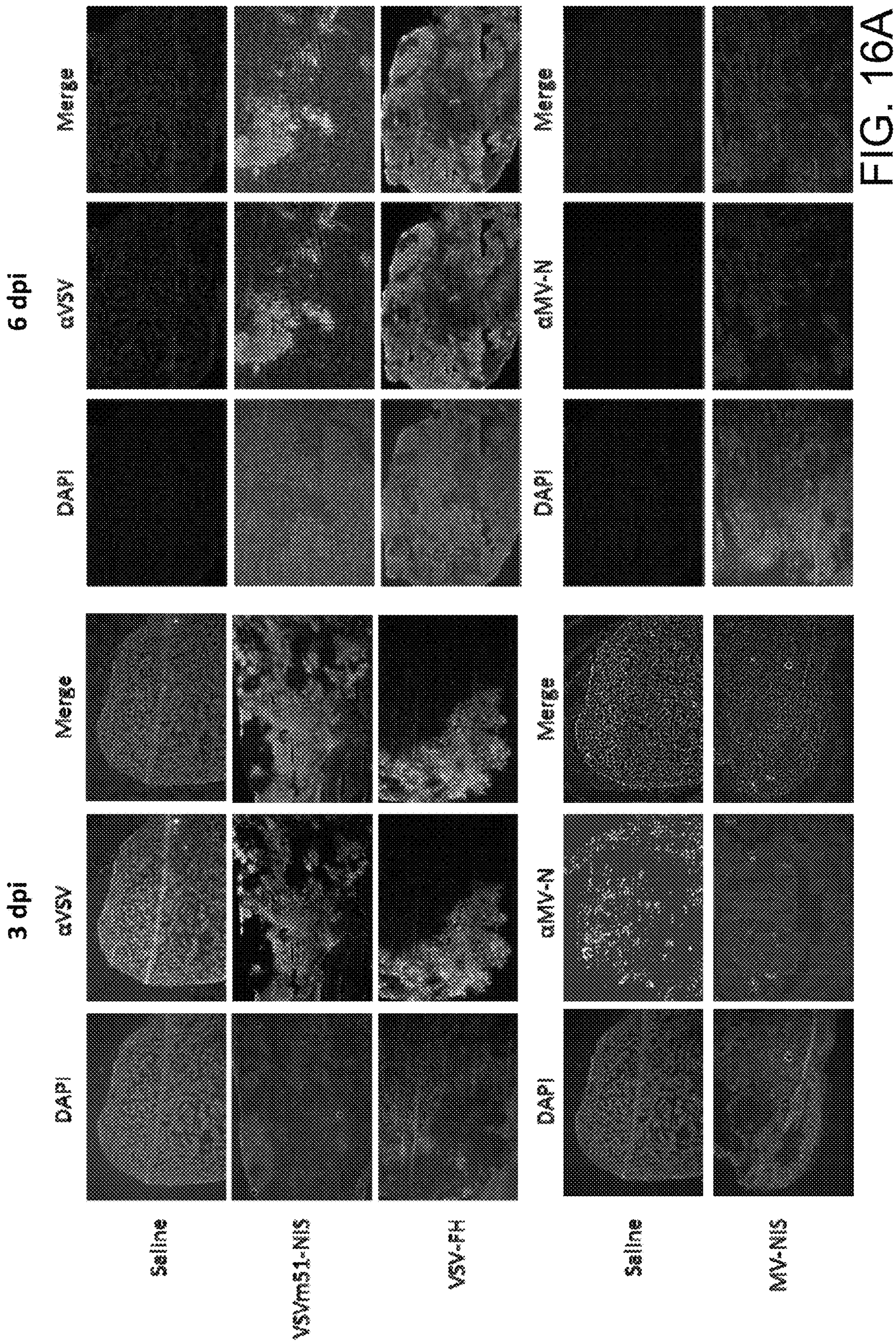
FIGS. 16A-16C. Evaluation of viral replication and spread in subcutaneous KAS 6/1 tumors. (a) Immunohistochemical staining for anti-VSV or anti-MV proteins and (b) viral titers in treated tumors at 3 and 6 days post intravenous delivery of the respective viruses. Individual $TCID_{50}$ calculations from three different tumors are shown. (c) Analysis of interferon alpha (IFNα) or beta (IFNβ) production by VSV (m51=VSV-M51, FH=VSV-FH) infected myeloma cell lines (mean±SEM, n=2).
Figure 16B:
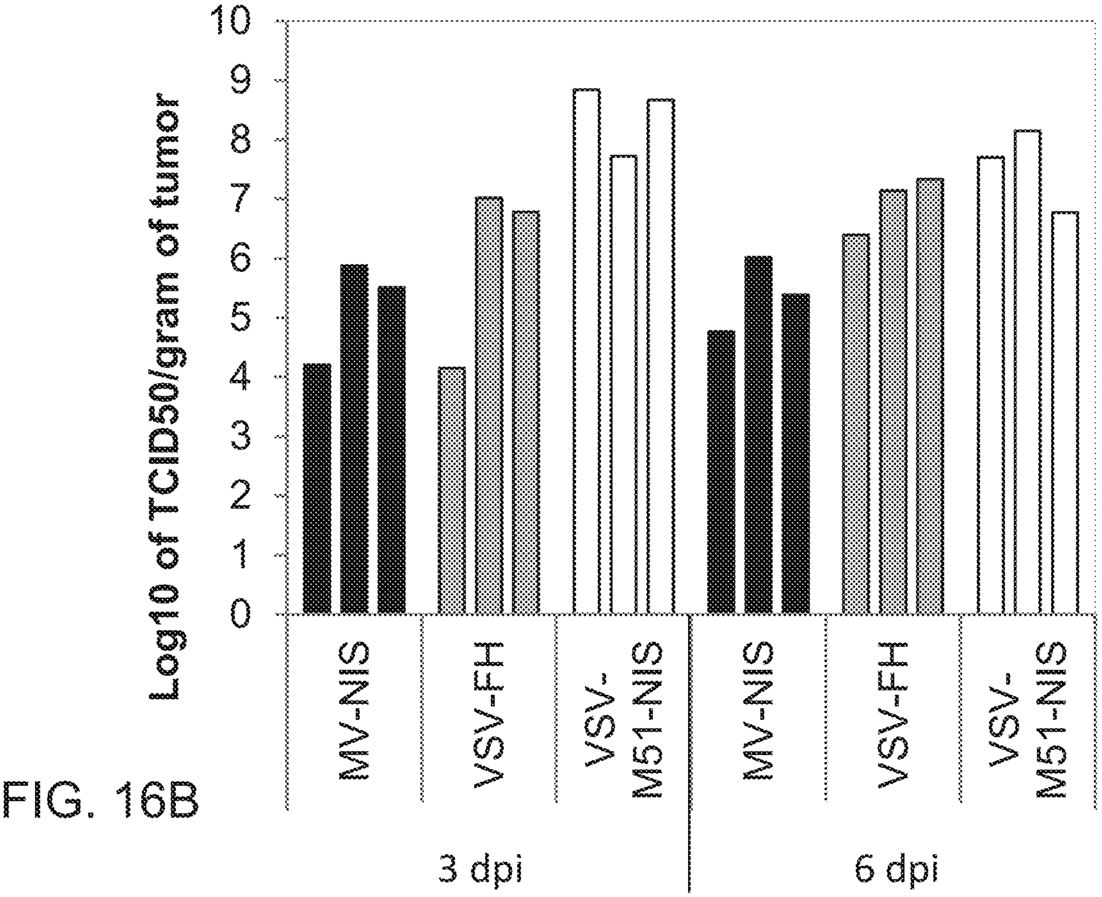
Figure 16C:
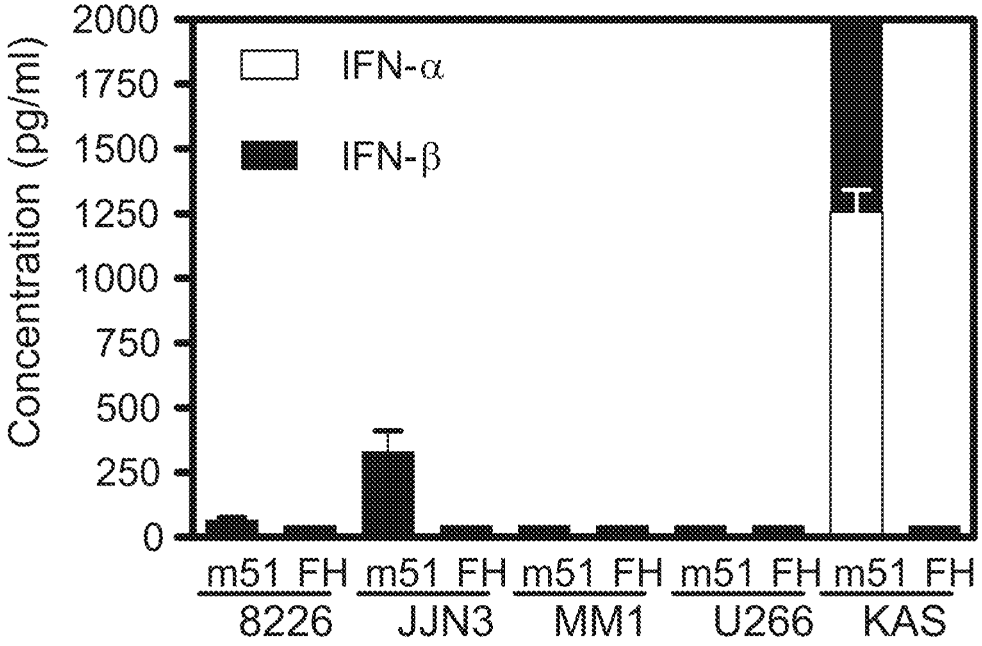

It is curious as to why VSV-M51-NIS was not potent against the myeloma cell line despite being highly active in vitro (FIG. 13). Hence, a cohort of mice was euthanized at day 3 and 6 to harvest tumors to enable analysis of viral replication by virus recovery assay ($TCID_{50}$/g tumor) or by immunohistochemical staining to show evidence of viral spread in the tumors. As observed in FIG. 16, there was good viral spread in the VSV-FH or VSV-M51-NIS treated mice at day 3. In contrast, since MV-NIS was a slower virus, there was only very weak staining at day 3. Quantitative measurements of virus replication were performed by recovery of infectious virus from tumors, confirming production of viral progeny in tumors post IV delivery of viruses (FIG. 16). However, it was also evident from the in vitro assay that KAS 6/1 cells produced abundant IFNα and IFNβ post infection by VSV-M51-NIS but not after infection by VSV-FH. Production of type I IFN may limit further viral spread in the in vivo setting.

These results demonstrate that a hybrid VSV/MV oncolytic virus can be generated as a systemic therapy for patients with multiple myeloma. Incorporation of MV envelope glycoproteins onto a VSV core yielded a stable fully replicative virus without the neurovirulence properties associated with VSV. VSV-FH, unlike the parental VSV-GFP, did not cause adverse clinical signs or weight loss when given intravenously to MV (CD46) receptor positive mice. The hybrid virus was fusogenic and acquired the tropism of MV, which included a preference for tumors expressing high levels of CD46, a complement regulatory protein that is overexpressed in a diversity of cancers while expressed at relatively low levels in normal cells. $CD138^+$ malignant plasma cells express 7-10 times higher CD46 on their cell surface compared to normal bone marrow stromal cells (Ong et al., *Exp. Hematol.*, 34:713-720 (2006)). Indeed, VSV-FH was able to efficiently infect primary $CD138^+$ myeloma cells and not $CD138^-$ normal bone marrow stromal cells. Compared to MV, VSV-FH replicated and spread faster with large syncytia. The faster replication of VSV-FH was evident in infection assays on Vero cells as well as in human cancer cell lines. A single dose of VSV-FH was able to induce rapid regression of subcutaneous KAS 6/1 tumors very early post treatment, an effect that was not observed in MV-NIS treated tumors despite mice given a 10-fold higher dose of MV-NIS.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A replication-competent vesicular stomatitis virus comprising an RNA molecule, wherein said RNA molecule comprises a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a Paramyxovirus F polypeptide, a nucleic acid sequence that is a template for a positive sense transcript encoding a Paramyxovirus H polypeptide, and a nucleic acid sequence that is a template for a positive sense transcript encoding a VSV L polypeptide, wherein said RNA molecule lacks a nucleic acid sequence that is a template for a positive sense transcript encoding a functional VSV G polypeptide.

2. The virus of claim 1, wherein said Paramyxovirus H polypeptide is a measles virus H polypeptide comprising Y481A and R533A amino acid substitutions with respect to a wild-type measles virus H polypeptide.

3. The virus of claim 1, wherein said Paramyxovirus H polypeptide comprises an amino acid sequence of a single chain antibody.

4. The virus of claim 3, wherein said single chain antibody is a single chain antibody directed to EGFR, αFR, or PSMA.

5. The virus of claim 1, wherein said RNA molecule virus comprises a nucleic acid sequence that is a template for a positive sense transcript encoding a NIS polypeptide.

6. A composition comprising a replication-competent vesicular stomatitis virus comprising RNA molecule, wherein said RNA molecule comprises a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a Paramyxovirus F polypeptide, a nucleic acid sequence that is a template for a positive sense transcript encoding a Paramyxovirus H polypeptide, and a nucleic acid sequence that is a template for a positive sense transcript encoding a VSV L polypeptide, wherein said RNA molecule lacks a nucleic acid sequence that is a template for a positive sense transcript encoding a functional VSV G polypeptide.

7. The composition of claim 6, wherein said Paramyxovirus H polypeptide is a measles virus H polypeptide comprising Y481A and R533A amino acid substitutions with respect to a wild-type measles virus H polypeptide.

8. The composition of claim 6, wherein said Paramyxovirus H polypeptide comprises an amino acid sequence of a single chain antibody.

9. The composition of claim 8, wherein said single chain antibody is a single chain antibody directed to EGFR, αFR, or PSMA.

10. The composition of claim 6, wherein said RNA molecule virus comprises a nucleic acid sequence that is a template for a positive sense transcript encoding a NIS polypeptide.

11. A nucleic acid molecule comprising a nucleic acid strand comprising a nucleic acid sequence that is a template for a positive sense transcript encoding a VSV N polypeptide, a nucleic acid sequence that is a template for a positive sense transcript encoding a VSV P polypeptide, a nucleic acid sequence that is a template for a positive sense transcript encoding a VSV M polypeptide, a nucleic acid sequence that is a template for a positive sense transcript encoding a Paramyxovirus F polypeptide, a nucleic acid sequence that is a template for a positive sense transcript encoding a Paramyxovirus H polypeptide, and a nucleic acid sequence that is a template for a positive sense transcript encoding a VSV L polypeptide, wherein said nucleic acid strand lacks a nucleic acid sequence that is a template for a positive sense transcript encoding a functional VSV G polypeptide.

12. The nucleic acid molecule of claim 11, wherein said nucleic acid strand comprises a nucleic acid sequence that is a template for a positive sense transcript encoding a NIS polypeptide.

13. The nucleic acid molecule of claim 12, wherein said NIS polypeptide is a human NIS polypeptide.

* * * * *